United States Patent [19]

Takada et al.

[11] Patent Number: 4,940,714
[45] Date of Patent: Jul. 10, 1990

[54] 2-SUBSTITUTED CARBONYLIMIDAZO[4,5-C]QUINOLINES

[75] Inventors: Susumu Takada, Hyogo; Toshio Fujishita, Osaka; Takashi Sasatani, Nara; Akira Matsushita, Hyogo; Masami Eigyo, Nara, all of Japan

[73] Assignee: Shionogi & Co., Ltd., Osaka, Japan

[21] Appl. No.: 309,868

[22] Filed: Feb. 14, 1989

[30] Foreign Application Priority Data

Feb. 16, 1988 [JP] Japan ................................. 63-33270

[51] Int. Cl.$^5$ ..................... C07D 471/04; A61K 31/47
[52] U.S. Cl. ........................................ 514/293; 546/82
[58] Field of Search ........................... 514/293; 546/82

[56] References Cited

U.S. PATENT DOCUMENTS

| | | | |
|---|---|---|---|
| 4,563,463 | 1/1986 | Musser et al. | 514/293 |
| 4,689,338 | 8/1987 | Gerster | 546/82 |
| 4,698,348 | 10/1987 | Gerster | 514/293 |
| 4,753,951 | 6/1988 | Takada et al. | 514/293 |

FOREIGN PATENT DOCUMENTS 0187705 7/1986 European Pat. Off. ............ 514/293
0223420 5/1987 European Pat. Off. .

OTHER PUBLICATIONS

Monatshefte für Chemie 111(4), 963–969 (1980), Base Induced Cyclization of Some Quinolines, CA 94(7):47216f.
J. Wiley, The Chemistry of Functional Groups, Part II, 1970, pp. 201–287 Entitled "Biochemistry and Pharmacology of the Nitro and Nitroso Groups".

*Primary Examiner*—Mary C. Lee
*Assistant Examiner*—Catherine S. Kilby Scalzo
*Attorney, Agent, or Firm*—Birch, Stewart, Kolasch & Birch

[57] ABSTRACT

2-Substituted carbonylimidazo[4,5-c]quinolines of formula:

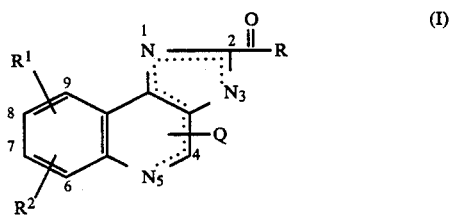

having a high affinity for benzodiazepin receptor and showing an excellent psychostimulating action orally at a dose of 0.1–500 mg are provided through several routes.

8 Claims, No Drawings

2-SUBSTITUTED CARBONYLIMIDAZO[4,5-C]QUINOLINES

BACKGROUND OF THE INVENTION

1. Field of the Invention

This invention relates to imidazo[4,5-c]quinolines substituted by a carbonyl group at the 2-position.

2. Prior Art

As to compounds having an imidazo[4,5-c]quinoline ring as a basic structure, Abbasi, et al. in Monatsh. Chem., 111, 963 (1980) have shown 3-hydroxy-2-hydroxymethyl-8-methoxy-9-nitro-4-styryl-2H-imidazo[4,5-c]quinoline derivatives as intermediates for synthesizing physiologically active substances. European Pat. No. 145,340 discloses 2-hydroxyalkyl-1H-imidazo[4,5-c]quinolines as bronchodilators or antiviral drugs.

SUMMARY

This invention relates to compounds of the formula:

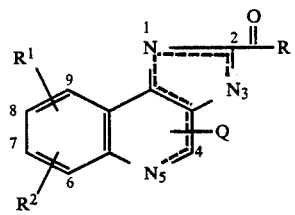

wherein R is (1) hydrogen; (2) hydroxy; (3) $C_1$–$C_{10}$ alkyl optionally substituted by halogen, $C_1$–$C_5$ alkylthio, $C_1$–$C_5$ alkoxycarbonyl, or phenyl; (4) $C_3$–$C_5$ cycloalkyl optionally substituted by $C_1$–$C_5$ alkyl; (5) $C_2$–$C_5$ alkenyl optionally substituted by $C_1$–$C_5$ alkyl or di-$C_1$–$C_5$ alkyl; (6) $C_1$–$C_5$ alkoxy; (7) phenoxy; (8) amino optionally substituted by $C_1$–$C_5$ alkyl or di-$C_1$–$C_5$ alkyl; (9) phenyl optionally substituted by one or two members independently selected from the group consisting of halogen, trifluoromethyl, $C_1$–$C_5$ alkoxy, and $C_1$–$C_5$ alkylthio; or (10) 5- or 6-membered heterocyclic group optionally substituted by one or two members independently selected from the group consisting of halogen, $C_1$–$C_5$ alkyl, and phenyl; Q is hydrogen, $C_1$–$C_5$ alkyl, benzyl, benzhydryl, trityl, $C_1$–$C_{13}$ acyl, $C_1$–$C_5$ alkylsulfonyl, or $C_6$–$C_{12}$ arylsulfonyl, provided that Q is located at nitrogen atom of 1-, 3-, or 5-position; $R^1$ and $R^2$ each is hydrogen, $C_1$–$C_5$ alkyl, $C_1$–$C_5$ alkoxy, or halogen; and the dotted lines indicate the presence of three double bonds at the position of 2(3), 3a(9b), 4(5); 1(9b), 2(3), 3a(4); or 1(2), 3a(9b), 4(5); or a pharmaceutically acceptable acid addition salt, and also relates to psychotropic agents containing the compound as an active ingredient.

DESCRIPTION OF THE PREFERRED EMBODIMENT

Compounds having the aforementioned basic structure have been widely studied. However, none of them were found to have any psychotropic activity. The present inventors have found that the above-mentioned imidazo[4,5-c]quinoline derivatives have utility as psychotropic agents (e.g. U.S. Pat. No. 4753951). In addition, they found that the compounds of the present invention having a carbonyl group at the 2-position have excellent psychotropic activity, based upon the activation of benzodiazepine receptors. Especially, these are expected as psychostimulants, based upon the potentiation of pentylenetetrazole (PTZ)-induced convulsions. So the compounds (I) of present invention may be useful for treatment of depression, convulsion, anxiety, amnesia, senile dementia, or cerebral disorders etc.

The terms used in the above definitions are explained below.

As the alkyl, there are exemplified straight or branched alkyl, such as methyl, ethyl, propyl, butyl, isobutyl, t-butyl, sec-butyl, pentyl, neopentyl, etc.

As the alkoxy, there are, for example, methoxy, ethoxy, propoxy, isopropoxy, butoxy, pentyloxy, etc.; and as the alkylthio, there are, for example, methylthio, ethylthio, propylthio, butylthio, isobutylthio, neopentylthio, etc.

As the cycloalkyl, there are exemplified cyclopropyl, cyclobutyl, cyclopentyl, cyclohexyl, cycloheptyl, etc.

As the alkenyl, there are, for example, vinyl, 1-propenyl, 2-propenyl, 1-isobutenyl, butenyl, isopentenyl, pentenyl, etc.

As the halogen, there are fluorine, chlorine, bromine and iodine.

As the 5- or 6-membered heterocyclic group, there are exemplified isoxazolyl, isothiazolyl, pyrazolyl, oxazolyl, thiazolyl, imidazolyl, thiadiazolyl, oxadiazolyl, thienyl, furyl, pyridyl, etc.

The compound (I) of the present invention can be obtained through the following four routes:

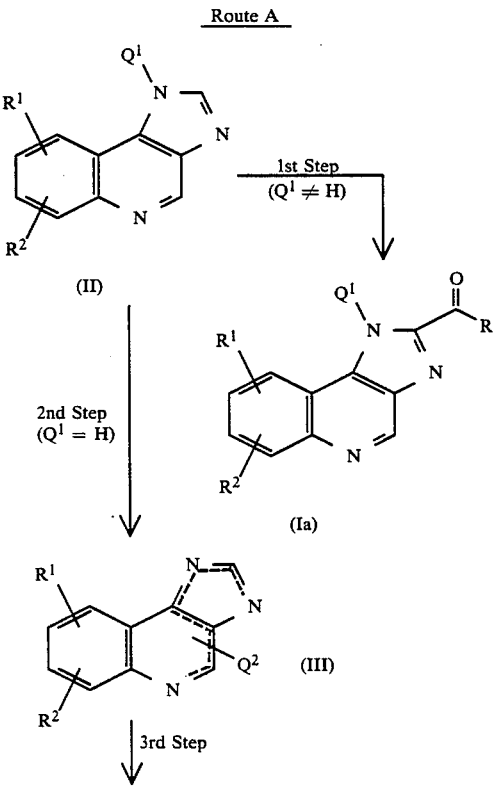

-continued
Route A

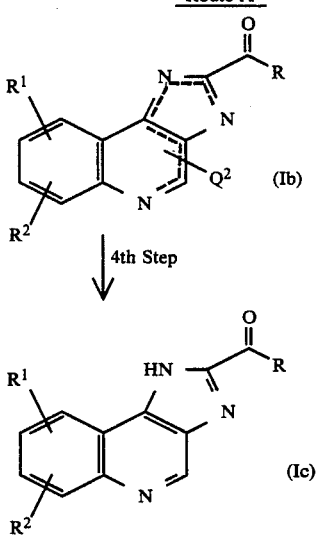

↓ 4th Step (wherein R, R¹ and R² have the same meaning as defined above; Q¹ is hydrogen or alkyl; and Q² is alkyl, benzyl, benzhydryl, or trityl.)

1ST STEP

The objective 2-carbonyl compound (Ia) is obtained by reacting the starting material (II) with an acylating agent or carbamoylating agent in the presence of a lithium-type base such as n-BuLi, sec-BuLi, t-BuLi, or PhLi. This reaction is carried out at a low temperature (about $-50 \sim$ about $-80°$ C.) usually in an appropriate solvent, using an acylating agent or carbamoylating agent corresponding to the required acyl or amide group, respectively.

As the solvent, ether-type solvents such as diethyl ether, diisopropyl ether, tetrahydrofuran, dioxane and 1,2-dimethoxyethane, etc. are exemplified.

As the acylating agent, acid halide, carboxylate, acid anhydride, mixed acid anhydride, etc. may be used.

As the carbamoylating agent, there may be used dimethylcarbamoyl halide and isocyanates such as alkyl isocyanate and phenyl isocyanate.

2ND STEP

The imidazo[4,5-c]quinoline (III) having a substituent at the 1-, 3-, or 5-position is obtained by reacting the starting material (II) with an appropriate alkylating agent for several hours in a suitable solvent in the presence of a base.

As the alkylating agent, there are, for example, alkyl halides such as methyl iodide and ethyl iodide; benzyl halides such as benzyl chloride; and benzhydryl bromide, trityl chloride, etc.

Comparatively bulky groups such as trityl are mainly introduced to the 3-position, while in case of less bulky alkyls such as methyl, ethyl, or propyl, compounds having substituents at the 1- or 5-position in addition to the 3-position are obtained as a mixture.

As the solvent, acetonitrile, tetrahydrofuran, ether, dioxane, dimethylformamide, etc. are exemplified.

As the base, triethylamine, pyridine, sodium ethylate, sodium hydride, etc are exemplified.

The reaction is completed in $5 \sim 30$ hours if performed at about $0° \sim$ about $50°$ C., preferably at room temperature.

3RD STEP

The objective compound (Ib) is obtained by acylating or carbamoylating the compound (III) in the same manner as in the 1st Step.

4TH STEP

The above-mentioned 2-carbonyl compound (Ib) is dealkylated by treating with a suitable reagent at about $0° \sim$ about $50°$ C., preferably at room temperature, whereby the objective compound (Ic) is obtained. As the reagent for dealkylation, trifluoroacetic acid, hydrogen iodide, boron tribromide, etc. are preferable.

Preparation of the Starting Material (II)

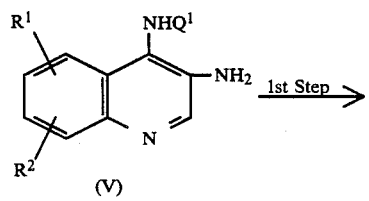

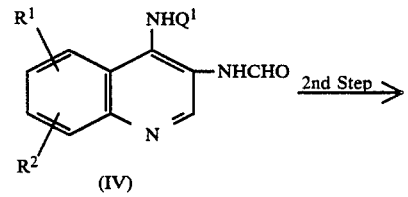

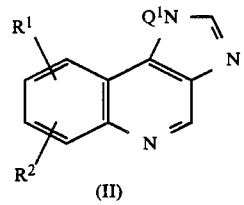

(Wherein R¹, R², and Q¹ have the same meanings as defined above.)

1ST STEP

4-Amino-3-formylaminoquinoline (IV) is obtained by reacting 3,4-diaminoquinoline (V) with formic acid under heating for several hours. The reaction may be carried out at about $80° \sim$ about $110°$ C. for 1-3 hours.

However, when Q¹ is not H, the compound (II) is directly obtained by this reaction in some cases.

2ND STEP

1H-Imidazo[4,5-c]quinoline compound (II) may be obtained by heating under reflux the above obtained compound (IV) obtained above in a solvent for several hours.

As the solvent, the solvents having high boiling point, for instance, alcohols such as ethylene glycol and ethers such as diglyme, and the like are exemplified.

The reaction may be carried out at about $100° \sim$ about $200°$ C. for 1-5 hours.

Route B

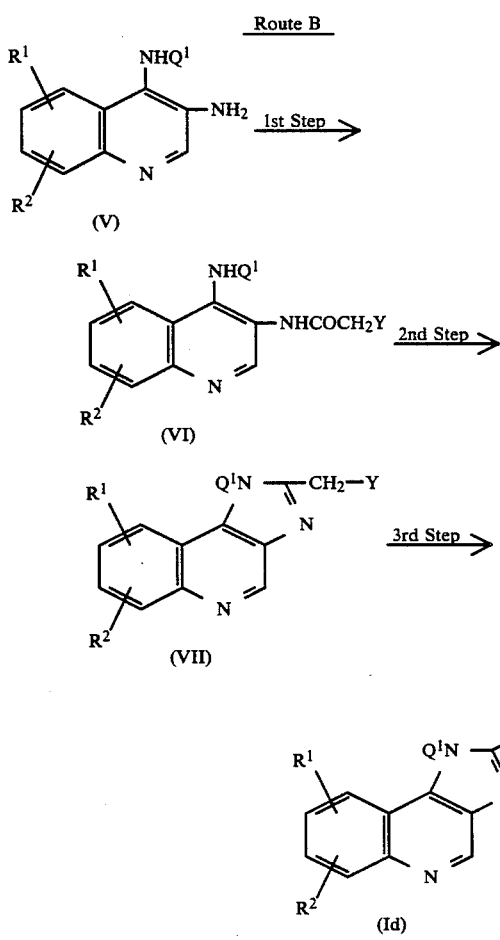

(wherein $R^1$, $R^2$, and $Q^1$ have the same meanings as defined above; Y is alkyl, cycloalkyl or aryl.)

1ST STEP

4-Amino-3-substituted acetamidoquinoline (VI) is obtained by reacting a substituted acetyl halide with the compound (V) in an appropriate solvent.

As the solvent, there are exemplified hexamethylphosphoramide, acetonitrile, dimethylformamide, chloroform or a mixture thereof.

The reaction is completed in 0.5~5.0 hours if performed at about $-50°$~about $5°$ C., preferably at about $-10°$~about $0°$ C.

2ND STEP

2-Substituted methyl-1H-imidazo[4,5-c]quinoline compound (VII) is obtained by heating the amide (VI) above for several minutes under reflux in a solvent.

As the solvent, solvents having high boiling point are preferable. They are, for instance, alcohols such as ethylene glycol, etc. and ethers such as diglyme, etc. The reaction is carried out for 10~40 minutes at about $100°$~about $200°$ C.

3RD STEP

The objective compound (Id) is obtained by heating the compound (VII) as obtained above with an oxidizing agent for several hours in an appropriate solvent.

As the solvent, dioxane, 1,2-dimethoxyethane, acetone, benzene, etc. are exemplified.

As the oxidizing agent, there are exemplified selenium dioxide, manganese dioxide, chromic anhydride, potassium permanganate, etc.

The reaction is completed in 1-3 hours if carried out at about $60°$~about $90°$ C.

Route C (When $R = OR^3$)

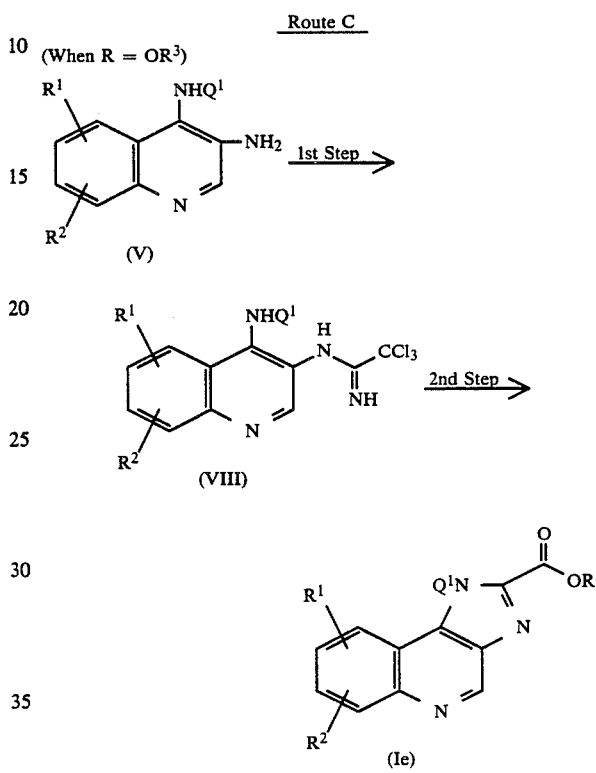

(wherein $R^1$, $R^2$, and $Q^1$ have the same meanings as defined above; $R^3$ is alkyl or aryl.)

1ST STEP

4-Amino-3-(trichloroacetimidoylamino)quinoline (VIII) is obtained by reacting methyltrichloroacetimidate with the compound (V) in an appropriate solvent, and then by stirring for several hours at room temperature.

As the solvent, acetic acid is preferable.

The reaction is carried out for 1-5 hours at about $0°$~about $50°$ C., preferably at room temperature.

2ND STEP

The objective compound (Ie) is obtained by reacting the compound (VIII) obtained above with a suitable alcohol or phenol under reflux or heating for several hours. As the alcohols there may be used, for example, methanol, ethanol, n-propyl alcohol, isopropyl alcohol, etc.

The phenols include cresols and naphthols as well as phenols.

The reaction is completed in 1-5 hours if carried out at about $60°$~about $200°$ C.

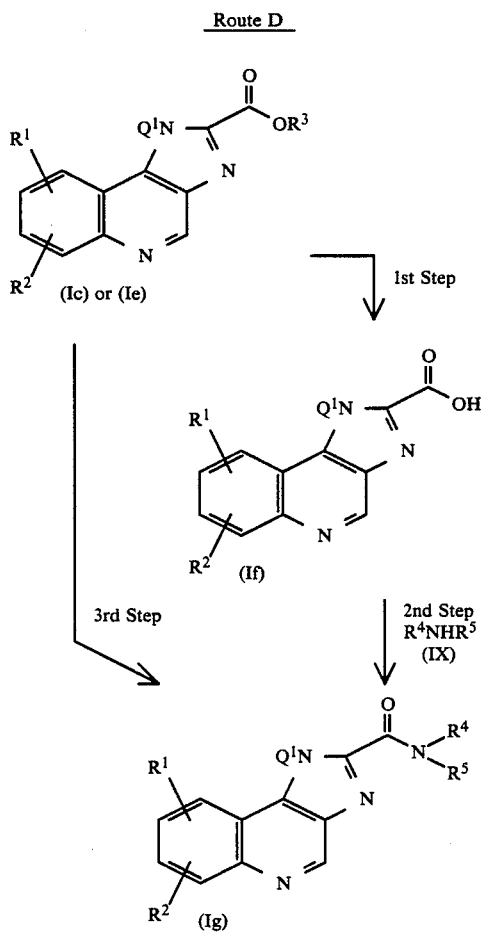

Route D (Ic) or (Ie)

1st Step (If)

2nd Step
R⁴NHR⁵
(IX)

3rd Step (Ig)

(wherein $R^1$, $R^2$, and $Q^1$ have the same meanings as defined above; $R^4$ and $R^5$ each is hydrogen or alkyl.)

1ST STEP

The carboxylic acid (If) is obtained by reacting the ester (Ic) or (Ie) with a base in an appropriate solvent for several hours.

As the solvent, there are exemplified methanol, ethanol, isopropanol, water or a mixture thereof. As the base, sodium hydroxide, potassium hydroxide, and the like are preferable.

This hydrolysis is carried out at about 10°~about 100° C. for 1–5 hours.

2ND STEP

The carboxylic acid (If) thus obtained is at first converted into an acid halogenide by the reaction with a halogenating agent such as thionyl chloride, etc. and the resulting halogenide is allowed to react with an appropriate amine (IX) to give the amide (Ig).

As the amines, there are exemplified N,N-dimethylamine, N,N-diethylamine, monomethylamine, monobutylamine, etc.

The reaction is carried out at about 0°~about 50° C., preferably at room temperature for 10~40 minutes. The reaction of the 2nd step may follow the 1st Step successively without isolation of the compound (If).

3RD STEP To a solution of the compound (Ic) or (Ie) in an appropriate solvent is added a suitable amine, and the mixture is heated at about 60°~about 150° C. for 1–5 hours in a sealed tube, whereby the objective compound (Ig) is obtained.

As the solvent, alcohols such as methanol and ethanol, etc. or water are exemplified.

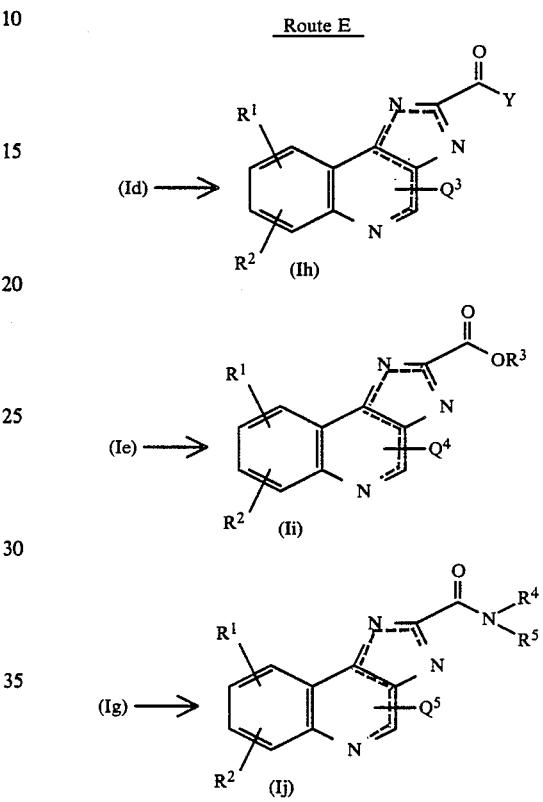

Route E (Id) → (Ih)

(Ie) → (Ii)

(Ig) → (Ij)

(wherein $Q^3$, $Q^4$, and $Q^5$ each is alkyl, acyl, alkylsulfonyl or arylsulfonyl; and $R^1$, $R^2$, $R^3$, $R^4$, $R^5$, and Y have the same meanings as defined above.)

The objective compound (Id), (Ie) and (Ig) obtained in the Routes B, C and D may be subjected to the reaction for indroducing substituent Q if Q' is hydrogen.

This reaction may be carried out by treating the compound (Id), (Ie) or (Ig) with a suitable reagent in the presence of a base for several hours in an appropriate solvent.

As the reagent, alkyl halide such as methyl iodide and ethyl iodide, etc.; acid halide, acid anhydride, sulfonyl chloride, etc. are exemplified.

As the solvent, there are, for example, acetonitrile, tetrahydrofuran, ether, dioxane, dimethylformamide, etc.

As the base, triethylamine, sodium alcoholate, sodium hydride, etc. are exemplified.

The reaction is completed in 5~30 hours if performed at about 0°~about 50° C., preferably at room temperature.

The objective compound (I) can be converted into its pharmaceutically acceptable acid addition salts such as salts with inorganic acids including hydrochloric acid, sulfuric acid, phosphoric acid, nitric acid, etc.; and organic acids including acetic acid, maleic acid, malic acid, citric acid, lactic acid, methanesulfonic acid, etc. The compounds (I) or the pharmaceutically acceptable acid addition salts show high affinities for benzodiazepine receptors and are useful as psychotropic agents such as psychostimulants or antianxiety agents.

The compounds (I) can be administered orally or parenterally to humans or mammals. They may be formulated in a conventional manner into tablets, capsules, pills, granules, injections, suppositories and syrups. The pharmaceutically acceptable carriers, diluents, and excipients illustratively include lactose, sucrose, wheat starch, potato starch, magnesium stearate, gelatin, methyl cellulose, agar, water and the like. If necessary, stabilizers, emulsifiers, wet extenders, buffers and other pharmaceutical auxiliaries may appropriately be added. An optimum daily dosage is 0.1~500 mg orally, and 0.1~300 mg injectably, in one to three divided doses.

The present invention is explained in more detail by the following Examples, Referential Examples, which are not intended to limit the scope of the invention.

The reactions shown in the Examples and Referential Examples are usually carried out in an anhydrous solvent under a nitrogen atomosphere. For the drying of extracting solvents, anhydrous magnesium or sodium sulfate is used. For chromatography on a column of silica gel, Kiesel gel 60 (70–230 mesh) made by Merck is used.

Abbreviations used in the Examples, Referential Examples and Tables have the following meanings:

Tr: trityl; Me: methyl; Et: ethyl; THF: tetrahydrofuran; MeOH: methanol, EtOH: ethanol; AcOEt: ethyl acetate; DMF: dimethylformamide; HMPA: hexamethylphosphoramide; MeCN: acetonitrile; (d): decomposition; (s): sublimation.

In the NMR spectrum, the indication of multiplicity is abbreviated as follows:

s: singlet; d: doublet; t: triplet; q: quartet; m:multiplet.

EXAMPLE 1

2-Cyclopropylcarbonyl-1H-imidazo[4,5-c]quinoline (Ic-1)

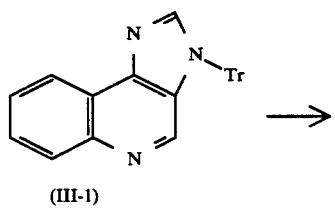

(III-1)

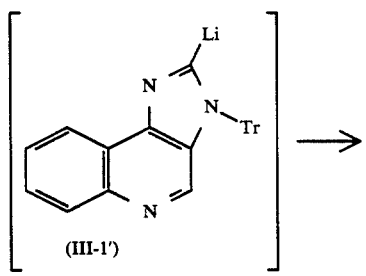

(III-1')

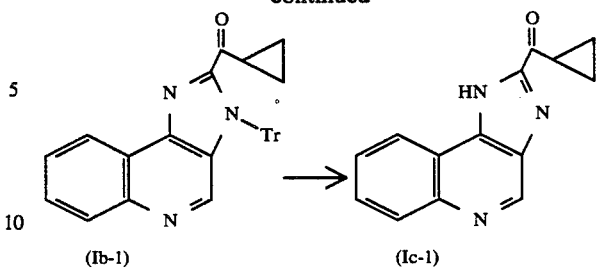

(Ib-1)　　　　　　(Ic-1)

To a cold solution (−70° C.) of 1.23 g of 3-trityl-3H-imidazo[4,5-c]quinoline (III-1) in 25 ml of THF was added dropwise a mixture of 3 ml of 1.6M solution of n-butyl lithium in hexane and 3 ml of THF while being kept at −72°~−68° C. The mixture was stirred at the same temperature for 30 min., whereby a yellow solution of 2-lithio form (III-1') was obtained. All the 2-lithio form used in the Examples hereafter are prepared according to the same reaction conditions. To the yellow solution of the compound (III-1') was added 1.04 g of cyclopropanecarbonyl chloride all at once. The temperature of the reaction solution was gradually elevated to room temperature, and the solvent was evaporated under reduced pressure. The residue was partitioned between ethyl acetate and aqueous ammonia. The organic layer was washed with water and saturated brine, successively, and dried. The ethyl acetate was removed by evaporation, and the residue was crystallized from n-hexane—ethyl acetate to give 900 mg of the crude crystals (Ib-1). The compound (Ib-1) was deprotected by mixing with 4 ml of trifluoroacetic acid. After stirring for 30 min. at room temperature, the reaction mixture was concentrated under reduced pressure, and the residue was partitioned between ethyl acetate and saturated aqueous sodium hydrogencarbonate. The organic layer was washed with water and saturated brine, and dried. The ethyl acetate was removed by evaporation, and the residue was chromatographed on a column of silica gel for purification. The fraction eluted with chloroform—methanol (30:1 v/v) was concentrated and crystallized from -hexane to give 395 mg (yield: 56%) of the titled compound (Ic-1). This was recrystallized from ethanol to give colorless crystals melting at 230° C. (dec.).

Anal. Calcd. (%) for $C_{14}H_{11}N_3O$ : C, 70.87; H, 4.67; N, 17.71. Found (%): C, 70.85; H, 4.84; N, 17.53.

NMR (DMSO-$d_6$) δ: 1.23 (4H, d), 3.35 (1H, quintet), 7.60~7.85 (2H, m), 8.05~8.25 (1H, m), 8.55~8.75 (1H, m), 9.33 (1H, s).

EXAMPLE 2

2-Isobutyryl-7-methoxy-1H-imidazo[4,5-c]quinoline (Ic-2)

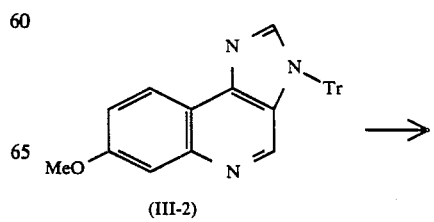

(III-2)

(Ib-2)

(Ic-2)

A solution of 1.32 g of 7-methoxy-3-trityl-3H-imidazo[4,5-c]quinoline (III-2) in 30 ml of THF was reacted with a mixture of 2.5 ml of 1.6M solution of n-butyl lithium in hexane and 2 ml of THF under the same conditions as in Example 1. To this was added 1.33 g of isobutyric anhydride. The reaction mixture was gradually warmed up to room temperature and concentrated under reduced pressure. The residue was partitioned between ethyl acetate and aqueous ammonia; and the organic layer was washed with water, then with saturated brine and dried. The ethyl acetate was removed by evaporation, and the residue was chromatographed on a column of silica gel for purification. The fraction eluted with ethyl acetate-n-hexane (1:2 v/v) was concentrated and crystallized from n-hexane to give 1.20 g of the objective compound (I b-2). The compound (I b-2) was dealkylated by mixing with 4 ml of trifluoroacetic acid. After treatment as in Example 1, the residue was chromatographed on a column of silica gel for purification. The fraction eluted with chloroform-methanol (30:1 v/v) was concentrated to give 580 mg (yield: 72%) of the titled compound (I c-2) as crystals. This was crystallized from ethanol to give colorless crystals melting at 283°~285° C.

Anal. Calcd. (%) for $C_{15}H_{15}N_3O_2$: C, 66,90; H, 5.61; N, 15.60. Found (%): C, 67.07; H, 5.56; N, 15.74.

NMR (DMSO-$d_6$) δ: 1.25 (6H, d), 3.93 (1H, septet), 3.97 (3H, s), 7.40 (1H, d, d), 7.57 (1H, d), 8.53 (1H, d), 9.28 (1H, s).

EXAMPLES 3~32

In the same manner as in Examples 1 or 2, the objective compounds (I c) were obtained under reaction conditions shown in Table 1. The physical properties of the objective compounds were shown in Tables 2-1 and 2-2.

TABLE 1

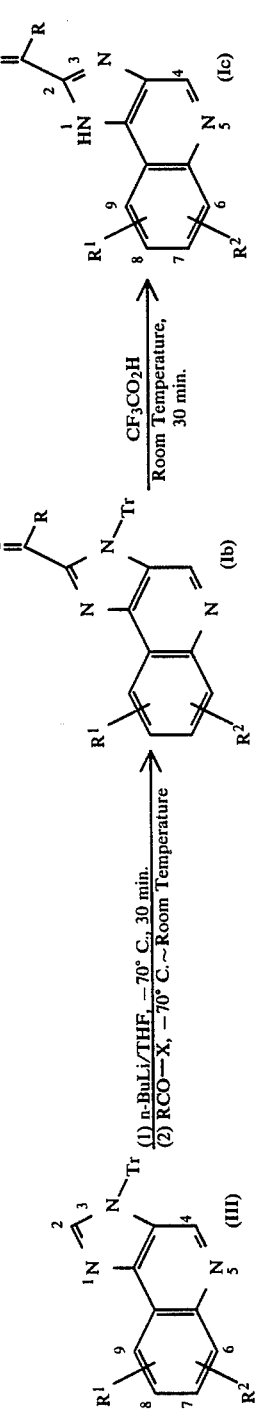

| Ex No. | R | R¹ | R² | Amount of Compd. (III) (g) | Solvent THF (ml) | 1st Step n-BuLi/THF (ml) | RCO—X (ml) | RCO—X | (g) | 2nd Step CF₃CO₂H (ml) | Yield (mg) | (%) | Compound (Ic) Compd. No. |
|---|---|---|---|---|---|---|---|---|---|---|---|---|---|
| 3 | —CH₃ | H | H | 1.23 | 30 | 4 | 4 | —OCOCH₃ | 1.3 | 6 | 290 | 46 | Ic-3 |
| 4 | —C₂H₅ | H | H | 1.23 | 25 | 2.5 | 2 | Cl | 0.75 | 4 | 295 | 44 | Ic-4 |
| 5 | —C₂H₅ | 7-OMe | H | 1.32 | 30 | 2.5 | 2 | Cl | 0.75 | 4 | 365 | 48 | Ic-5 |
| 6 | —(CH₂)₂CH₃ | H | H | 1.23 | 25 | 2.5 | 2 | —OCO(CH₂)₂CH₃ | 1.26 | 4 | 265 | 37 | Ic-6 |
| 7 | —(CH₂)₃CH₃ | H | H | 1.23 | 25 | 2.5 | 2 | —OCO(CH₂)₃CH₃ | 1.50 | 4 | 450 | 61 | Ic-7 |
| 8 | —(CH₂)₄CH₃ | H | H | 1.23 | 25 | 2.5 | 2 | —OCO(CH₂)₄CH₃ | 1.85 | 4 | 355 | 44 | Ic-8 |
| 9 | —(CH₂)₅CH₃ | H | H | 1.23 | 25 | 2.5 | 2 | —OCO(CH₂)₅CH₃ | 2.10 | 4 | 580 | 69 | Ic-9 |
| 10 | —(CH₂)₆CH₃ | H | H | 1.23 | 25 | 2.5 | 2 | Cl | 1.33 | 4 | 240 | 27 | Ic-10 |
| 11 | —(CH₂)₇CH₃ | H | H | 1.23 | 25 | 2.5 | 2 | Cl | 1.47 | 3 | 260 | 29 | Ic-11 |
| 12 | —(CH₂)₈CH₃ | H | H | 1.23 | 25 | 2.5 | 2 | Cl | 1.56 | 4 | 270 | 28 | Ic-12 |
| 13 | —(CH₂)₉CH₃ | H | H | 1.23 | 25 | 2.5 | 2 | Cl | 1.65 | 4 | 290 | 29 | Ic-13 |
| 14 | —CH(CH₃)₂ | H | H | 1.23 | 25 | 2.5 | 2 | —OCOCH(CH₃)₂ | 0.95 | 4 | 150 | 21 | Ic-14 |
| 15 | —CH(CH₃)₂ | 7-F | H | 1.42 | 25 | 2.8 | 2 | Cl | 0.94 | 3 | 124 | 15 | Ic-15 |
| 16 | —CH(CH₃)₂ | 8-F | H | 1.29 | 70 | 2.5 | 2 | Cl | 0.85 | 4 | 240 | 31 | Ic-16 |
| 17 | —CH(CH₃)₂ | 8-Me | H | 1.27 | 27 | 2.5 | 2 | —OCOCH(CH₃)₂ | 1.33 | 4 | 550 | 73 | Ic-17 |
| 18 | —CH(CH₃)(C₂H₅) | H | H | 1.23 | 25 | 2.5 | 2 | Cl | 0.99 | 4 | 350 | 46 | Ic-18 |
| 19 | —CH₂CH(CH₃)₂ | H | H | 1.23 | 25 | 2.5 | 2 | —OCOCH₂CH(CH₃)₂ | 1.50 | 4 | 470 | 62 | Ic-19 |
| 20 | ▽ | 7-F | H | 1.72 | 80 | 3.2 | 2 | Cl | 1.07 | 3 | 430 | 42 | Ic-20 |
| 21 | ▽ | 8-F | H | 1.72 | 80 | 3.2 | 2.5 | Cl | 1.07 | 4 | 580 | 57 | Ic-21 |
| 22 | ▽ | 7-OMe | H | 1.32 | 30 | 2.5 | 2 | Cl | 1.04 | 4 | 460 | 58 | Ic-22 |

TABLE 1-continued
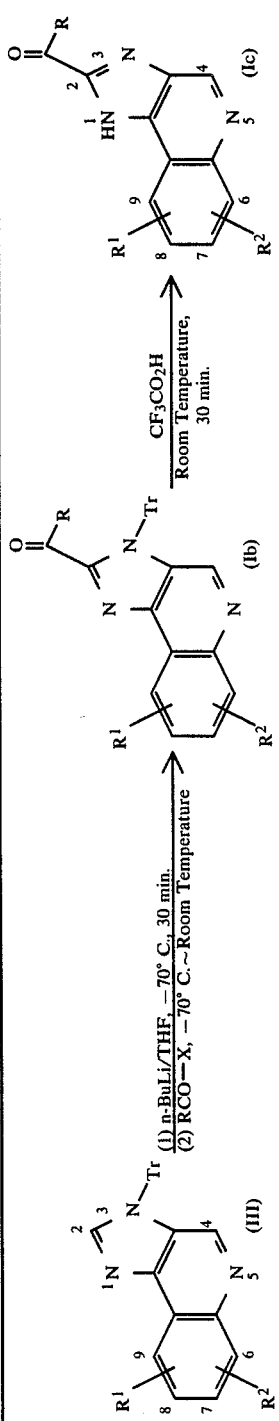
| Ex No. | R | R¹ | R² | Amount of Compd. (III) (g) | Solvent THF (ml) | 1st Step n-BuLi-THF (ml) | (ml) | RCO—X X | (g) | 2nd Step CF₃CO₂H (ml) | Yield (mg) | (%) | Compd. No. |
|---|---|---|---|---|---|---|---|---|---|---|---|---|---|
| 23 | cyclopropyl | 8-Me | H | 1.27 | 27 | 2.5 | 2 | Cl | 1.04 | 4 | 425 | 57 | Ic-23 |
| 24 | 1-methylcyclopropyl | H | H | 1.23 | 25 | 2.5 | 2 | Cl | 0.95 | 3 | 350 | 47 | Ic-24 |
| 25 | cyclobutyl | H | H | 1.23 | 25 | 2.5 | 2 | Cl | 1.50 | 3 | 300 | 40 | Ic-25 |
| 26 | cyclopentyl | H | H | 1.23 | 25 | 2.5 | 2 | Cl | 1.00 | 4 | 290 | 37 | Ic-26 |
| 27 | (E)-propenyl | H | H | 1.23 | 25 | 2.5 | 2 | Cl | 0.93 | 4 | 100 | 14 | Ic-27 |
| 28 | (E)-2-butenyl | H | H | 1.23 | 25 | 2.5 | 2 | Cl | 0.90 | 2 | 110 | 15 | Ic-28 |
| 29 | 2-methyl-2-butenyl | H | H | 1.23 | 25 | 2.5 | 2 | Cl | 0.96 | 3 | 350 | 47 | Ic-29 |

TABLE 1-continued
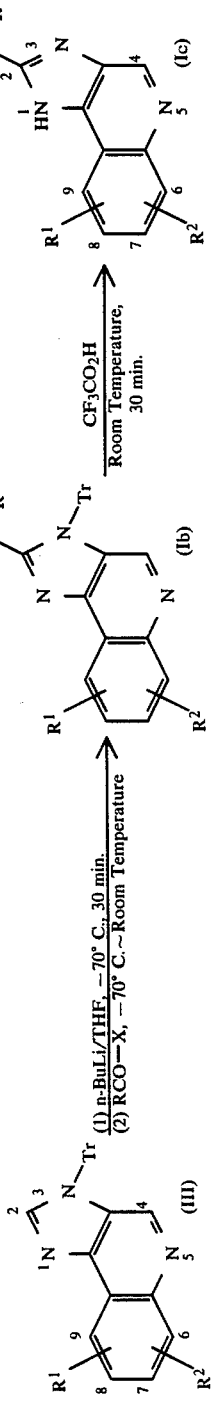
| Ex No. | R | R¹ | R² | Amount of Compd. (III) (g) | 1st Step Solvent THF (ml) | n-BuLi-THF (ml) | (ml) | RCO—X X | RCO—X (g) | 2nd Step CF₃CO₂H (ml) | Compound (Ic) Yield (mg) | Yield (%) | Compd. No. |
|---|---|---|---|---|---|---|---|---|---|---|---|---|---|
| 30 | —(CH₂)₃Cl | H | H | 1.23 | 25 | 2.5 | 2 | Cl | 1.13 | 2 | 120 | 15 | Ic-30 |
| 31 | —(CH₂)₂SCH₃ | H | H | 1.23 | 25 | 2.5 | 2 | Cl | 2.00 | 2 | 160 | 20 | Ic-31 |
| 32 | —(CH₂)₂-⌬ | H | H | 1.23 | 25 | 2.5 | 2 | Cl | 1.20 | 2 | 195 | 22 | Ic-32 |

TABLE 2

![Structure (Ic): Quinoline with HN-CH(R³)-C(=O)-R at position 4, R¹ at position 7/8, R² at position 6, numbering 1-9 with N at position 5]

(Ic)

| Compd. No. | R¹ | R² | R | m.p. (°C.) | Appearance | Recrystallizing Solvent | Molecular Formula | Elementary Analysis (%) Up (Calcd.), Down (Found) C | H | N | NMR (DMSO-d6) δ |
|---|---|---|---|---|---|---|---|---|---|---|---|
| Ic-3 | H | H | —CH₃ | 247–250(d) | Colorless | EtOH | C₁₂H₉N₃O | 68.24 / 67.99 | 4.29 / 4.35 | 19.89 / 19.56 | 2.80 (3H, s), 7.60~7.90 (2H, m), 8.05~8.75 (1H, m), 9.33 (1H, s) |
| Ic-4 | H | H | —C₂H₅ | 230(d) | Colorless | EtOH | C₁₃H₁₁N₃O | 69.32 / 69.41 | 4.92 / 4.99 | 18.65 / 18.56 | 1.20 (3H, t), 3.27 (2H, q), 8.60~8.90 (2H, m), 8.05~8.25 (1H, m), 8.55~8.75 (1H, m), 9.32 (1H, s) |
| Ic-5 | 7-OMe | H | —C₂H₅ | 295(d) | Light yellow | EtOH—CHCl₃ | C₁₄H₁₃N₃O₂ | 65.87 / 65.71 | 5.13 / 5.23 | 16.46 / 16.45 | 1.18 (3H, t), 3.27 (2H, q), 3.93 (3H, s), 7.37 (1H, d, d), 7.57 (1H, d), 8.53 (1H, d), 9.27 (1H, s) |
| Ic-6 | H | H | —(CH₂)₂CH₃ | 236–238 | Colorless | EtOH | C₁₄H₁₃N₃O | 70.26 / 70.27 | 5.48 / 5.57 | 17.56 / 17.51 | 0.98 (3H, t), 1.55~1.98 (2H, t), 3.25 (2H, t), 7.65~7.90 (2H, m), 8.05~8.30 (1H, m), 8.55~8.80 (1H, m), 9.33 (1H, s) |
| Ic-7 | H | H | —(CH₂)₃CH₃ | 229–231 | Colorless | EtOH | C₁₅H₁₅N₃O | 71.13 / 71.36 | 5.97 / 6.05 | 16.59 / 16.60 | 0.93 (3H, t), 1.15~1.90 (4H, m), 3.27 (2H, t), 7.65~7.90 (2H, m), 8.10~8.35 (1H, m), 8.55~8.80 (1H, m), 9.33 (1H, s) |
| Ic-8 | H | H | —(CH₂)₄CH₃ | 214–216 | Colorless | AcOEt | C₁₆H₁₇N₃O | 71.89 / 72.14 | 6.41 / 6.48 | 15.72 / 15.70 | 0.90 (3H, t), 1.10~1.90 (6H, m), 3.25 (2H, t), 7.60~7.90 (2H, m), 8.05~8.30 (1H, m), 8.55~8.80 (1H, m), 9.33 (1H, s) |
| Ic-9 | H | H | —(CH₂)₅CH₃ | 205–206 | Colorless | EtOH | C₁₇H₁₉N₃O | 72.57 / 72.64 | 6.81 / 6.77 | 14.93 / 14.97 | 0.87 (3H, t), 1.00~1.95 (8H, m), 3.27 (2H, t), 7.60~7.90 (2H, m), 8.10~8.30 (1H, m), 8.55~8.75 (1H, m), 9.33 (1H, s) |
| Ic-10 | H | H | —(CH₂)₆CH₃ | 196–198 | Colorless | EtOH | C₁₀H₂₁N₃O | 73.19 / 73.21 | 7.17 / 7.18 | 14.23 / 14.18 | 0.87 (3H, t), 1.15~2.00 (10H, m), 3.27 (2H, t), 7.65~7.95 (2H, m), 8.05~8.30 (1H, m), 8.55~8.80 (1H, m), 9.33 (1H, s) |
| Ic-11 | H | H | —(CH₂)₇CH₃ | 193–195 | Colorless | EtOH—CHCl₃ | C₁₉H₂₃N₃O | 73.76 / 73.75 | 7.49 / 7.49 | 13.58 / 13.57 | 0.83 (3H, t), 1.05~1.90 (12H, m), 3.25 (2H, t), 7.65~7.95 (2H, m), 8.05~8.25 (1H, m), 8.55~8.75 (1H, m), 9.33 (1H, s) |
| Ic-12 | H | H | —(CH₂)₈CH₃ | 190–192 | Colorless | EtOH | C₂₀H₂₅N₃O | 74.27 / 74.63 | 7.79 / 7.86 | 12.99 / 13.03 | 0.83 (3H, t), 1.05~1.90 (14H, m), 3.23 (2H, t), 7.65~7.90 (2H, m), 8.05~8.25 (1H, m), 8.55~8.75 (1H, m), 9.30 (1H, s) |
| Ic-13 | H | H | —(CH₂)₉CH₃ | 185–186 | Colorless | EtOH | C₂₁H₂₇N₃O | 74.74 / 74.96 | 8.06 / 8.10 | 12.45 / 12.46 | 0.83 (3H, t), 1.05~1.95 (16H, m), 3.25 (2H, t), 7.65~7.90 (2H, m), 8.10~8.30 (1H, m), 8.55~8.75 (1H, m), 9.33 (1H, s) |
| Ic-14 | H | H | —CH(CH₃)₂ | 274–276 | Colorless | EtOH | C₁₄H₁₃N₃O | 70.26 / 70.27 | 5.48 / 5.60 | 17.56 / 17.59 | 1.27 (6H, d), 3.98 (1H, septet), 7.70~7.90 (2H, m), 8.05~8.30 (1H, m), 8.55~8.80 (1H, m), 9.35 (1H, s) |
| Ic-15 | 7-F | H | —CH(CH₃)₂ | 278–281(d) | Colorless | MeOH—AcOEt | C₁₄H₁₂N₃OF | 65.36 / 65.33 | 4.70 / 4.74 | 16.33 / 16.25 | F 7.38 / F 7.41 | 1.27 (6H, d), 3.96 (1H, septet), 7.62~7.73 (1H, m), 7.87 (1H, d), 8.64~8.71 (1H, m), 9.35 (1H, s) |
| Ic-16 | 8-F | H | —CH(CH₃)₂ | 250–252(d) | Colorless | AcOEt—CH₂Cl₂ | C₁₄H₁₂N₃OF | 65.36 / 65.44 | 4.70 / 4.96 | 16.33 / 16.13 | F 7.38 / F 7.49 | 1.27 (6H, d), 3.96 (1H, septet), 7.61~7.71 (1H, m), 8.18~8.25 (1H, m), 8.30~8.43 (1H, m), 9.31 (1H, s) |

TABLE 2-continued (Ic structure: quinoline with R¹ at 8-position, R² at 6-position, NH-CH₂-C(=O)-R substituent at 4-position)

| Compd. No. | R¹ | R² | R | m.p. (°C.) | Appearance | Recrystallizing Solvent | Molecular Formula | Elementary Analysis (%) Up (Calcd.), Down (Found) | | | | NMR (DMSO-d₆) δ |
|---|---|---|---|---|---|---|---|---|---|---|---|---|
| | | | | | | | | C | H | N | | |
| Ic-17 | 8-Me | H | —CH(CH₃)₂ | 231–232 | Light yellow | EtOH | $C_{15}H_{15}N_3O$ | 71.13 / 71.30 | 5.97 / 6.10 | 16.59 / 16.54 | | 1.30 (6H, d), 3.97 (1H, septet), 7.55 (1H, d, d), 8.03 (1H, d), 8.40 (1H, d), 9.23 (1H, s) |
| Ic-18 | H | H | —CH(CH₃)(C₂H₅) | 243–244 | Colorless | EtOH—CHCl₃ | $C_{15}H_{16}N_3O$ | 71.13 / 71.09 | 5.97 / 6.07 | 16.59 / 16.41 | | 0.93 (3H, t), 1.25 (3H, d), 1.40~2.05 (2H, m), 3.55~4.10 (1H, m), 7.65~7.90 (2H, m), 8.10~8.30 (1H, m), 8.60~8.80 (1H, m), 9.37 (1H, s) |
| Ic-19 | H | H | —CH₂CH(CH₃)₂ | 259–261 | Colorless | EtOH | $C_{15}H_{15}N_3O$ | 71.13 / 71.32 | 5.97 / 6.10 | 16.59 / 16.49 | | 1.00 (6H, d), 2.33 (1H, septet), 3.15 (2H, d), 7.65~7.90 (2H, m), 8.10~8.30 (1H, m), 8.55~8.75 (1H, m), 9.33 (1H, s) |
| Ic-20 | 7-F | H | cyclopropyl | 267–270 | Colorless | MeOH—CHCl₃ | $C_{14}H_{16}N_3OF$ | 65.87 / 65.81 | 3.94 / 4.13 | 16.46 / 16.38 | F 7.44 / 7.59 | 1.23~1.27 (4H, m), 3.28~3.43 (1H, m), 7.62~7.72 (1H, m), 7.87~7.94 (1H, m), 8.64~8.71 (1H, m), 9.36 (1H, s) |
| Ic-21 | 8-F | H | cyclopropyl | 273(d) | Colorless | MeOH—AcOEt | $C_{14}H_{10}N_3OF$ | 65.87 / 65.95 | 3.94 / 4.08 | 16.46 / 16.56 | F 7.33 / 7.32 | 1.24~1.28 (4H, m), 3.30~3.46 (1H, m), 7.60~7.71 (1H, m), 8.18~8.25 (1H, m), 8.31~8.38 (1H, m), 9.30 (1H, s) |
| Ic-22 | 7-OMe | H | cyclopropyl | 285(d) | Colorless | EtOH—CHCl₃ | $C_{15}H_{13}N_3O_2$ | 67.41 / 67.56 | 4.90 / 4.95 | 15.72 / 15.77 | | 1.20 (4H, d), 3.37 (1H, quintet), 3.93 (3H, s), 7.37 (1H, d, d), 7.58 (1H, d), 8.53 (1H, d), 9.30 (1H, s) |
| Ic-23 | 8-Me | H | cyclopropyl | 245(d) | Colorless | EtOH | $C_{15}H_{13}N_3O$ | 71.70 / 71.86 | 5.21 / 5.23 | 16.72 / 16.86 | | 1.23 (4H, m), 3.40 (1H, quintet), 3.57 (3H, s), 7.60 (1H, d, d), 8.05 (1H, d), 8.43 (1H, d), 9.27 (1H, s) |
| Ic-24 | H | H | —CH(CH₃)-cyclopropyl | 241–243(d) | Colorless | EtOH | $C_{15}H_{12}N_3O$ | 71.99 / 71.96 | 4.83 / 5.22 | 16.79 / 16.75 | | 1.00~1.90 (6H, m), 3.05~3.40 (1H, m), 7.60~7.90 (2H, m), 8.05~8.30 (1H, m), 8.50~8.75 (1H, m), 9.35 (1H, s) |
| Ic-25 | H | H | cyclobutyl | 246–248(d) | Colorless | EtOH | $C_{15}H_{13}N_3O$ | 71.70 / 71.83 | 5.21 / 5.30 | 16.72 / 16.59 | | 1.80~2.40 (6H, m), 4.23~4.60 (1H, m), 7.60~7.90 (2H, m), 8.05~8.30 (1H, m), 8.55~8.75 (1H, m), 9.30 (1H, s) |

TABLE 2-continued

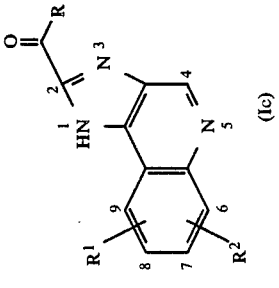
(Ic)

| Compd. No. | R¹ | R² | R | m.p. (°C.) | Appearance | Recrystallizing Solvent | Molecular Formula | Elementary Analysis (%) Up (Calcd.), Down (Found) | | | | NMR (DMSO-d$_6$) δ |
|---|---|---|---|---|---|---|---|---|---|---|---|---|
| | | | | | | | | C | H | N | | |
| Ic-26 | H | H | cyclopentyl | 264(d) | Colorless | EtOH | C$_{16}$H$_{15}$N$_3$O | 72.43<br>72.72 | 5.70<br>5.80 | 15.84<br>15.79 | | 1.50~2.30 (8H, m), 4.00~4.45 (1H, m), 7.65~7.90 (2H, m), 8.10~8.30 (1H, m), 8.55~8.75 (1H, m), 9.35 (1H, s) |
| Ic-27 | H | H | CH=C(CH$_3$)$_2$ | 224(d) | Light yellow | EtOH—CHCl$_3$ | C$_{14}$H$_{11}$N$_3$O | 70.87<br>70.93 | 4.67<br>4.69 | 17.71<br>17.67 | | 2.07 (3H, d), 7.30~7.95 (4H, m), 8.05~8.30 (1H, m), 8.55~8.80 (1H, m), 9.33 (1H, s) |
| Ic-28 | H | H | CH=CH—CH$_3$ (trans) | 225-227 | Colorless | EtOH | C$_{14}$H$_{11}$N$_3$O | 70.87<br>70.93 | 4.67<br>4.81 | 17.71<br>17.48 | | 2.10 (3H, s), 6.27~6.40 (1H, m), 7.27 (1H, s), 7.65~7.95 (2H, m), 8.05~8.30 (1H, m), 8.55~8.70 (1H, m), 9.33 (1H, s) |
| Ic-29 | H | H | C(CH$_3$)=CH—CH$_3$ | 272(d) | Colorless | EtOH—CHCl$_3$ | C$_{15}$H$_{13}$N$_3$O | 71.70<br>71.87 | 5.21<br>5.30 | 16.72<br>16.68 | | 2.11 (3H, s), 2.35 (3H, s), 7.40~7.50 (1H, m), 7.60~7.85 (2H, m), 8.05~8.25 (1H, m), 8.50~8.75 (1H, m), 9.30 (1H, s) |
| Ic-30 | H | H | —(CH$_2$)$_3$Cl | 175(d) | Colorless | EtOH | C$_{14}$H$_{12}$N$_3$OCl | 61.43<br>61.44 | 4.42<br>4.41 | 15.35<br>15.17 | Cl 12.95<br>Cl 13.09 | 2.20 (2H, t, t), 2.47 (2H, t), 2.80 (2H, t), 7.60~7.95 (2H, m), 8.10~8.30 (1H, m), 8.55~8.75 (1H, m), 9.35 (1H, s) |
| Ic-31 | H | H | —(CH$_2$)$_2$SCH$_3$ | 210(d) | Colorless | EtOH | C$_{14}$H$_{13}$N$_3$OS | 61.97<br>61.97 | 4.83<br>4.76 | 15.49<br>15.23 | S 11.82<br>S 11.60 | 2.15 (3H, s), 2.93 (2H, t), 3.57 (2H, t), 7.65~7.90 (2H, m), 8.05~8.30 (1H, m), 8.55~8.80 (1H, m), 9.33 (1H, s) |
| Ic-32 | H | H | —(CH$_2$)$_2$—C$_6$H$_5$ | 251-253 | Colorless | EtOH | C$_{19}$H$_{15}$N$_3$O | 75.73<br>75.94 | 5.02<br>5.16 | 13.94<br>14.02 | | 3.07 (2H, t), 3.60 (2H, t), 7.05~7.45 (5H, m), 7.60~7.90 (2H, m), 8.00~8.25 (1H, m), 8.50~8.75 (1H, m), 9.30 (1H, s) |

EXAMPLE 33

2-(4-Methoxycarbonylbutylyl)-1H-imidazo[4,5-c]quinoline (I c-33)

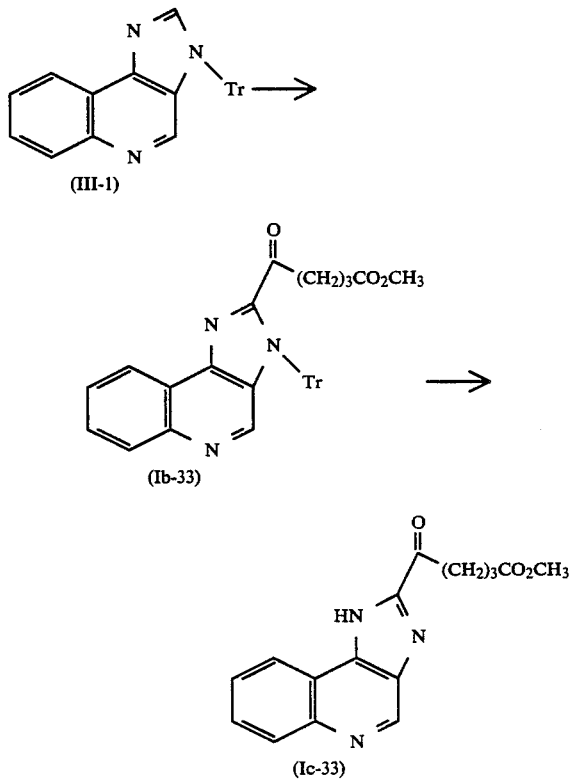

To a mixture of 1.23 g of trityl compound (III-1) in 25 ml of THF and a solution of 2.5 ml of n-butyl lithium-2 ml of THF prepared in the same manner as in Example 1 was added 1.30 g of glutaric acid dimethyl ester. The mixture was stirred for 30 min. at −70° C. and 240 mg of acetic acid was added thereto. The reaction solution was elevated to room temperature and concentrated under reduced pressure. The residue obtained was distributed in ethyl acetate-saturated aqueous sodium hydrogencarbonate. The organic layer was washed with water and saturated brine, successively, and dried. The ethyl acetate was removed by evaporation, and the residue was chromatographed on a column of silica gel eluting with ethyl acetate-n-hexane (1:2 v/v) to give an oily substance (I b-33). The oily substance (I b-33) obtained was dealkylated by mixing with 4 ml of trifluoroacetic acid. After treating in the same manner as in Example 1, the residue was chromatographed on a column of silica gel for purification. The fraction eluted with chloroform-methanol (30:1 v/v) was concentrated and crystallized from n-hexane to give 245 mg (yield: 28%) of the titled compound (I c-33). This was crystallized from ethanol to give colorless crystals melting at 207°∼208° C.

Anal. Calcd. (%) for $C_{16}H_{15}N_3O_3$: C, 64.64; H, 5.09; N, 14.13. Found (%): C, 64.68; H, 5.09; N, 13.99.

NMR (DMSO-d$_6$)δ: 1.98 (2H, t, t), 2.47 (2H, t), 3.33 (2H, t), 3.63 (3H, s), 7.65∼7.90 (2H, m), 8.05∼8.25 (1H, m), 8.55∼8.75 (1H, m), 9.30 (1H, s).

EXAMPLE 34

2-Formyl-1H-imidazo[4,5-c]quinoline (I c-34)

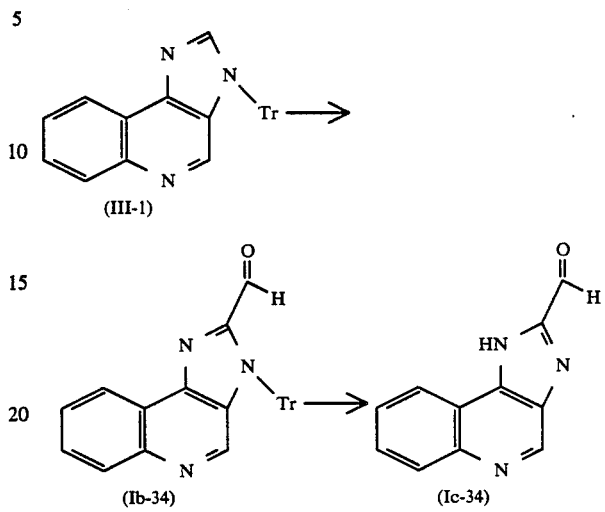

To a mixture of 1.23 g of trityl compound (III-1) in 25 ml of THF and a solution of 2.5 ml of 1.6M solution of n-butyl litium in hexane −2 ml of THF prepared in the same manner as in Example 1 was added dropwise 760 mg of DMF. After stirring the reaction mixture for 30 min. at −70° C., 240 mg of acetic acid was added thereto, and the tempera-ture of the mixture was elevated to room temperature. After treating in the same manner as in Example 33, the residue was chromatographed on a column of silica gel eluting with ethyl acetate-n-hexane (1:2 v/v) to give an oily substance (I b-34). The oily substance (I b-34) obtained was dealkylated by mixing with 4 ml of trifluoroacetic acid. The reaction mixture was concentrated under reduced pressure. Saturated aqueous sodium hydrogencarbonate was added to the residue, and the resulting precipitate was collected by filtration, washed with water and dried. This was chromatographed on a column of silica gel eluting with ethyl acetate-methanol (20:3 v/v). The fraction ob-tained was concentrated and crystallized from ethanol to give 210 mg (yield: 36%) of the titled compound (I c-34). This was crystallized from DMF to give colorless crystals melting at 254° C. (d).

Anal. Calcd. (%) for $C_{11}H_7N_3O.1/10 H_2O$ : C, 66.39; H, 3.65; N, 21.12.
Found (%): C, 66.27; H, 3.87; N, 20.86.
Mass spectrum: m/z 197 (M+).
NMR (DMSO-d$_6$)δ: 7.60∼7.95 (2H, m), 8,10∼8.30 (2H, m), 8.50∼8.70 (1H, m), 9.37 (1H, s), 10.08 (1H, s).

EXAMPLE 35

2-(4-Fluorobenzoyl)-1H-imidazo[4,5-c]quinoline (I c-35)

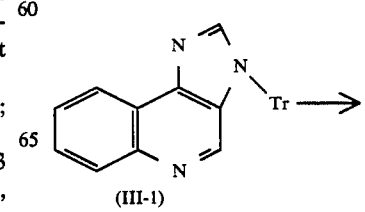

-continued

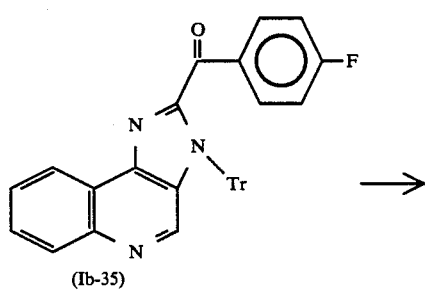
(Ib-35)

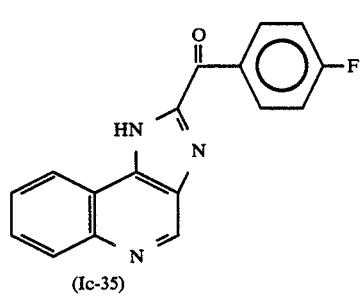
(Ic-35)

EXAMPLE 36

2-[(5-Chlorothiophen-2-yl)carbonyl]-1H-imidazo[4,5-c]quinoline (I c-36)

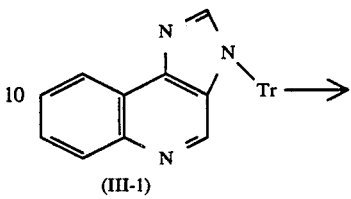
(III-1)

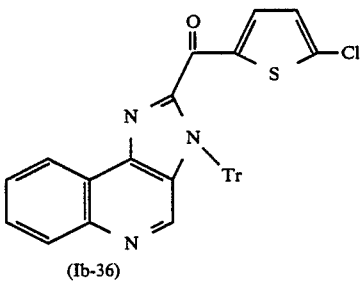
(Ib-36)

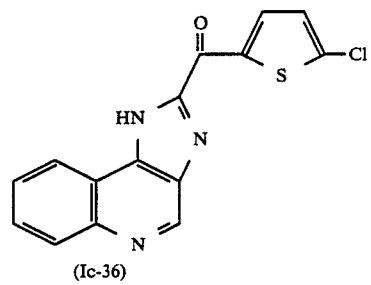
(Ic-36)

To a mixture of 1.64 g of trytyl compound (III-1) in 20 ml of THF and a solution of 4 ml of n-butyl lithium and 10 ml of THF was added 2.55 g of 4-fluorobenzoic acid chloride. The reaction solution was −10 ml of THF was added 2.55 g of 4-fluorobenzoyl chloride. The reaction mixture was warmed to room temperature and concentrated under reduced pressure. The residue was partitioned between ethyl acetate and aqueous ammonia. The organic layer was washed with water, then with brine and dried. The ethyl acetate was removed by evaporation and an oily substance obtained was chromatographed on a column of silica gel eluting with ethyl acetate-n-hexane (1:2 v/v). The fraction obtained was concentrated and crystallized from n-hexane to give 1.36 g of the titled compound (I b-35). The compound (I b-35) was suspended in 6 ml of trifluoroacetic acid and stirred for 30 min. at room temperature. The reaction mixture was concentrated under reduced pressure, and the residue was neutralized with saturated aqueous sodium hydrogencarbonate. The precipitate obtained was collected by filtration, washed with water and dried. This material was chromatographed on a column of silica gel eluting with chloroform-methanol (30:1 v/v) to give 740 mg (yield: 64%) of the titled compound (I c-35). This was recrystallized from ethanol-chloroform to give light yellow crystals melting at 305°~307° C.

Anal. Calcd. (%) for $C_{17}H_{10}N_3OF$ : C, 70.10; H, 3.46; N, 14.43; F, 6.52. Found (%): C, 70.25; H, 3.70; N, 14.34; F, 6.62.

NMR (DMSO-d$_6$)δ: 7.30~7.95 (4H, m), 8.10~8.30 (1H, m), 8.57~8.90 (3H, m), 9.40 (1H, s).

A solution of 1.4 g of methyl 5-chloro-2-thiophencarboxylate in 2 ml of THF was added dropwise to a solution prepared in the same manner as in Example 1 from a solution of 1.23 g of the compound (III-1) in 25 ml of THF and a mixture of 2.5 ml of 1.6M solution of n-butyl lithium in hexane −2 ml of THF. After stirring for 30 min., 240 mg of acetic acid was added thereto, and the temperature was elevated to room temperature. After workup in the same manner as in Example 33, the residue was chromatographed on a column of silica gel eluting with ethyl acetate-n-hexane (1:2 v/v). The fraction was concentrated to give an oily substance (I b-36). The oily substance (I b-36) was dealkylated by mixing with 4 ml of trifluoroacetic acid. Crude crystals obtained by the same workup as in Example 35 were chromatographed on a column of silica gel for purification. When the fraction eluted with chloroform-methanol (30:1 v/v) was concentrated and crystallized from ethanol, 560 mg (yield: 61%) of the titled compound (I c-36) was obtained. This was recrystallized from ethanol-chloroform to give light yellow crystals melting at 320°-322° C.

Anal. Calcd. (%) for $C_{15}H_8N_3OSCl$ :C, 57.42; H, 2.57; N, 13.39; S, 10.22; Cl, 11.30. Found (%): C, 57.17; H, 2.77; N, 13.17; S, 10.17; Cl, 11.24.

NMR (DMSO-d$_6$)δ: 7.38 (1H, d), 7.60~7.90 (2H, m), 8.05~8.25 (1H, m), 8.53 (1H, d), 8.55~8.80 (1H, m), 9.33 (1H, s).

EXAMPLES 37~63

In the same manner as in Examples 35 or 36, the objective compounds (I c) were obtained under the reaction conditions shown in Table 3. The physical properties of the compounds were shown in Tables 4-1 and 4-2.

TABLE 3

(III-1) → (1) n-BuLi/THF, −70° C. 30 min. / (2) RCO—X, −70° ~ Room Temperature → (Ib) → CF$_3$CO$_2$H, Room Temperature, 30 min. → (Ic)

| | | 1st Step | | | | | 2nd Step | Compound (Ic) | | |
|---|---|---|---|---|---|---|---|---|---|---|
| Ex No | R | Amount of Compd. (III-1) (g) | Solvent THF (ml) | n-BuLi-THF (ml) | | RCO—X | Solvent THF (ml) | CF$_3$CO$_2$H (ml) | Yield from (III-1) | Compd. No. |
| | | | | | | X (g) | | | (mg) (%) | |
| 37 | 2-F-phenyl | 1.23 | 30 | 3 | 3 | Cl 1.59 | — | 5 | 370 43 | Ic-37 |
| 38 | 3-F-phenyl | 1.23 | 25 | 3 | 3 | Cl 1.56 | — | 4 | 450 52 | Ic-38 |
| 39 | 2,4-diF-phenyl | 1.23 | 25 | 2.5 | 2 | Cl 1.44 | — | 4 | 350 38 | Ic-39 |
| 40 | 3-CF$_3$-phenyl | 1.23 | 30 | 4 | 4 | Cl 2.60 | — | 10 | 545 53 | Ic-40 |
| 41 | 4-Cl-phenyl | 0.82 | 20 | 3 | 3 | Cl 1.77 | — | 5 | 180 29 | Ic-41 |
| 42 | 2-Cl-phenyl | 1.23 | 25 | 4 | 4 | Cl 2.35 | — | 5 | 295 32 | Ic-42 |

TABLE 3-continued (III-1) [imidazo-quinoline-Tr compound]

(1) n-BuLi/THF, −70° C. 30 min.
(2) RCO—X, −70°~Room Temperature
→ (Ib)

CF₃CO₂H, Room Temperature, 30 min.
→ (Ic)

| Ex No | R | 1st Step Amount of Compd. (III-1) (g) | Solvent THF (ml) | n-BuLi-THF (ml) | (ml) | RCO—X X | (g) | Solvent THF (ml) | 2nd Step CF₃CO₂H (ml) | Compound (Ic) Yield from (III-1) (mg) | (%) | Compd. No. |
|---|---|---|---|---|---|---|---|---|---|---|---|---|
| 43 | phenyl-Cl | 1.23 | 25 | 2.5 | 2 | Cl | 1.50 | — | 4 | 460 | 50 | Ic-43 |
| 44 | phenyl-OMe | 1.23 | 25 | 4 | 4 | Cl | 2.20 | — | 6 | 600 | 66 | Ic-44 |
| 45 | phenyl-SMe | 1.23 | 25 | 2.5 | 2 | OMe | 1.32 | 4 ml | 4 | 560 | 59 | Ic-45 |
| 46 | phenyl-Me | 1.23 | 25 | 4 | 4 | Cl | 1.99 | — | 6 | 410 | 48 | Ic-46 |
| 47 | phenyl-Me | 1.23 | 25 | 2.5 | 2 | Cl | 1.29 | — | 4 | 520 | 61 | Ic-47 |
| 48 | pyridyl | 1.23 | 25 | 2.5 | 2 | OEt | 1.20 | — | 4 | 420 | 51 | Ic-48 |
| 49 | pyridyl | 1.23 | 25 | 2.5 | 2 | OEt | 1.30 | 2 ml | 4 | 300 | 37 | Ic-49 |
| 50 | cyclopentadienyl | 1.23 | 25 | 4 | 4 | OEt | 1.98 | — | 5 | 300 | 36 | Ic-50 |

TABLE 3-continued

Reaction scheme: Compound (III-1) → (Ib) → (Ic)

(1) n-BuLi/THF, −70° C. 30 min.
(2) RCO—X, −70° ~ Room Temperature

CF₃CO₂H, Room Temperature, 30 min.

|       |   | 1st Step | | | | | | 2nd Step | Compound (Ic) | | |
|-------|---|----------|---|---|---|---|---|----------|---|---|---|
|       |   | Amount of Compd. (III-1) | Solvent | n-BuLi-THF | | RCO—X | | Solvent | CF₃CO₂H | Yield from (III-1) | | Compd. |
| Ex No | R | (g) | THF (ml) | (ml) | (ml) | X | (g) | THF (ml) | (ml) | (mg) | (%) | No. |
| 51 | S (thiophene) | 1.23 | 25 | 2 | 2 | Cl | 0.70 | 2 ml | 4 | 310 | 37 | Ic-51 |
| 52 | S-Cl (chlorothiophene) | 1.23 | 25 | 2.5 | 2 | OMe | 1.40 | 2 ml | 2 | 100 | 11 | Ic-52 |
| 53 | Me-substituted | 1.23 | 25 | 2.5 | 2 | OMe | 1.25 | 2 ml | 4 | 430 | 49 | Ic-53 |
| 54 | Me-thiophene | 1.23 | 25 | 2.5 | 2 | OMe | 1.25 | 2 ml | 8 | 500 | 57 | Ic-54 |
| 55 | Me- | 1.23 | 25 | 2.5 | 2 | Cl | 1.30 | — | 4 | 530 | 60 | Ic-55 |
| 56 | O (furan) | 1.23 | 25 | 2.5 | 2 | Cl | 1.06 | — | 5 | 415 | 53 | Ic-56 |
| 57 | Me- | 1.23 | 25 | 2.5 | 2 | OMe | 1.15 | — | 4 | 425 | 51 | Ic-57 |
| 58 | O (furan) | 1.23 | 25 | 2.5 | 2 | Cl | 1.04 | — | 4 | 485 | 62 | Ic-58 |
| 59 | O (furan) | 1.95 | 30 | 3 | 3 | Cl | 1.26 | — | 4 | 115 | 9 | Ic-59 |

TABLE 3-continued

[Reaction scheme: Compound (III-1), an N-trityl imidazo-quinoline, treated with (1) n-BuLi/THF, −70° C. 30 min.; (2) RCO—X, −70° ~ Room Temperature, giving compound (Ib) which bears a —C(=O)R group on the imidazole and N-Tr; then treated with CF₃CO₂H, Room Temperature, 30 min., to give compound (Ic) with free NH.]

| Ex No | R | 1st Step Amount of Compd. (III-1) (g) | Solvent THF (ml) | n-BuLi-THF (ml) | (ml) | RCO—X X | (g) | Solvent THF (ml) | 2nd Step CF₃CO₂H (ml) | Compound (Ic) Yield from (III-1) (mg) | (%) | Compd. No. |
|---|---|---|---|---|---|---|---|---|---|---|---|---|
| 60 | [3-methyl-5-Me isoxazol-4-yl] | 1.23 | 25 | 3 | 3 | Cl | 1.40 | — | 6 | 470 | 57 | Ic-60 |
| 61 | [3-Me isoxazol-5-yl] | 1.23 | 25 | 2.5 | 2 | Cl | 1.40 | 4 ml | 4 | 140 | 17 | Ic-61 |
| 62 | [2-Me oxazol-5-yl] | 1.23 | 25 | 2 | 2 | OEt | 1.00 | 2 ml | 2 | 220 | 26 | Ic-62 |
| 63 | [2-Me pyrrol-5-yl] | 1.23 | 25 | 2.5 | 2 | OEt | 1.40 | 2 ml | 4 | 220 | 25 | Ic-63 |

TABLE 4

(Ic structure: quinoline with HN-C(=O)-R substituent)

| Compd. No. | R | m.p. (°C.) | Appearance | Recrystalli-zing Solvent | Molecular Formula | Elementary Analysis (%) Up (Calcd.) Down (Found) C H N | | | | NMR (DMSO-d₆) δ |
|---|---|---|---|---|---|---|---|---|---|---|
| Ic-37 | 2-F-phenyl | 263–265 | Light yellow | EtOH | C₁₇H₁₀N₃OF | 70.10 69.85 | 3.46 3.68 | 14.43 14.38 | F 6.52 F 6.64 | 7.30~7.97 (5H,m), 8.00~8.33 (2H,m), 8.53~8.80 (1H,m), 9.37 (1H,s) |
| Ic-38 | 3-F-phenyl | 306–308 | Light yellow | EtOH—CHCl₃ | C₁₇H₁₀N₃OF | 70.10 70.20 | 3.46 3.76 | 14.43 14.41 | F 6.52 F 6.58 | 7.55~7.95 (4H,m), 8.07~8.27 (1H,m), 8.30~8.53 (2H,m), 8.60~8.80 (1H,m), 9.40 (1H,s) |
| Ic-39 | 2,4-diF-phenyl | 287–289(d) | Light yellow | EtOH—CHCl₃ | C₁₇H₉N₃OF₂ | 66.02 66.03 | 2.93 3.16 | 13.59 13.55 | F 12.29 F 12.26 | 7.20~7.90 (4H,m), 8.10~8.45 (2H,m), 8.55~8.85 (1H,m), 9.33 (1H,s) |
| Ic-40 | 3-CF₃-phenyl | 252–253 | Colorless | EtOH—CHCl₃ | C₁₈H₁₀N₃OF₃ | 63.85 63.50 | 2.95 3.07 | 12.31 12.37 | F 16.70 F 16.45 | 7.70~8.30 (5H,m), 8.60~8.80 (1H,m), 8.83~9.03 (2H,m), 9.40 (1H,s) |
| Ic-41 | 4-Cl-phenyl | 310(s) | Yellow | EtOH—CHCl₃ | C₁₇H₁₀N₃OCl | 66.35 66.61 | 3.28 3.29 | 13.65 13.66 | Cl 11.52 Cl 11.33 | 7.60~7.90 (4H,m), 8.05~8.25 (1H,m), 8.55~8.80 (3H,m), 9.37 (1H,s) |

TABLE 4-continued

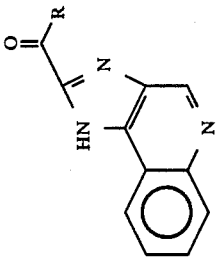
(Ic)

| Compd. No. | R | m.p. (°C.) | Appearance | Recrystalli- zing Solvent | Molecular Formula | Elementary Analysis (%) Up (Calcd.) Down (Found) | | | | NMR (DMSO-d6) δ |
|---|---|---|---|---|---|---|---|---|---|---|
| | | | | | | C | H | N | | |
| Ic-42 | 2-Cl-phenyl | 298-300(d) | Light yellow | EtOH—CHCl3 | C17H10N3OCl | 66.35 66.04 | 3.28 3.58 | 13.65 13.35 | Cl 11.52 Cl 11.42 | 7.50~8.00 (6H,m), 8.15~8.30 (1H,m), 8.50~8.80 (1H,m), 9.33 (1H,s) |
| Ic-43 | 3-Cl-phenyl | 283-285 | Light yellow | EtOH—CHCl3 | C17H10N3OCl | 66.35 66.43 | 3.28 3.34 | 13.65 13.65 | Cl 11.52 Cl 11.82 | 7.60~7.95 (4H,m), 8.10~8.35 (1H,m), 8.50~8.80 (3H,m), 9.40 (1H,s) |
| Ic-44 | 4-OMe-phenyl | 274-276 | Colorless | EtOH | C18H13N3O2 | 71.28 71.39 | 4.32 4.30 | 13.85 13.79 | | 3.93 (3H,s), 7.20 (2H,d), 7.65~7.93 (2H,m), 8.05~8.30 (1H,m), 8.60~8.85 (3H,m), 9.40 (1H,s) |
| Ic-45 | 4-SMe-phenyl | 275-277 | Light yellow | EtOH—CHCl3 | C18H13N3OS | 67.69 67.88 | 4.10 4.26 | 13.16 13.06 | S 10.04 S 9.92 | 2.60 (3H,s), 7.47 (2H,d), 7.65~7.90 (2H,m), 8.10~8.30 (1H,m), 8.55~8.80 (3H,m), 9.37 (1H,s) |
| Ic-46 | 4-Me-phenyl | 286-287 | Light yellow | EtOH—CHCl3 | C18H13N3O | 75.25 75.17 | 4.56 4.59 | 14.62 14.52 | | 2.45 (3H,s), 7.45 (2H,d), 7.65~7.90 (2H,m), 8.07~8.30 (1H,m), 8.50~8.80 (3H,m), 9.37 (1H,s) |

TABLE 4-continued (Ic) structure: HN-R group on quinoline with -C(O)-R substituent

| Compd. No. | R | m.p. (°C.) | Appearance | Recrystallizing Solvent | Molecular Formula | Elementary Analysis (%) Up (Calcd.) Down (Found) C  H  N | NMR (DMSO-d6) δ |
|---|---|---|---|---|---|---|---|
| Ic-47 | 3-Me-phenyl | 246–248 | Colorless | EtOH | $C_{18}H_{13}N_3O$ | 75.25 4.56 14.62 / 75.72 4.83 14.57 | 2.47 (3H,s), 7.45~7.90 (4H,m), 8.05~8.80 (4H,m), 9.40 (1H,s) |
| Ic-48 | 4-pyridyl | 311–312 | Yellow | EtOH—CHCl$_3$ | $C_{16}H_{10}N_4O$ | 70.07 3.68 20.43 / 70.02 3.86 20.22 | 7.65~7.90 (2H,m), 8.10~8.30 (1H,m), 8.33~8.47 (2H,m), 8.60~8.80 (1H,m), 8.90~9.05 (2H,m), 9.40 (1H,s) |
| Ic-49 | 3-pyridyl | 330–333(d) | Yellow | EtOH—CHCl$_3$ | $C_{16}H_{10}N_4O$ | 70.07 3.68 20.43 / 70.36 3.91 20.39 | 7.60~7.90 (3H,m), 8.10~8.25 (1H,m), 8.65~9.00 (3H,m), 9.40 (1H,s), 9.63~9.80 (1H,m) |
| Ic-50 | 2-thienyl | 315–317(d) | Colorless | EtOH—CHCl$_3$ | $C_{15}H_9N_3OS$ | 64.50 3.25 15.04 S 11.48 / 64.36 3.38 14.81 S 11.27 | 7.30~7.45 (1H,m), 7.60~7.90 (2H,m), 8.05~8.33 (2H,m), 8.55~8.90 (2H,m), 9.37 (1H,s) |
| Ic-51 | 3-thienyl | 300–302 | Yellow | EtOH—CHCl$_3$ | $C_{15}H_9N_3OS$ | 64.50 3.25 15.04 S 11.48 / 64.50 3.43 14.99 S 11.39 | 7.65~7.90 (3H,m), 7.95~8.30 (2H,m), 8.63~8.80 (1H,m), 9.37 (1H,s), 9.40~9.50 (1H,m) |
| Ic-52 | 5-chloro-2-thienyl | 335(d) | Yellow | DMF | $C_{15}H_8N_3OSCl$ | 57.42 2.57 13.39 S 10.22, Cl 11.30 / 57.29 2.83 13.41 S 10.26, Cl 11.44 | 7.65~7.90 (2H,m), 7.97 (1H,d), 8.05~8.30 (1H,m), 8.65~8.80 (1H,m), 9.25 (1H,d), 9.35 (1H,s) |

TABLE 4-continued

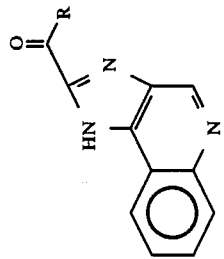

(Ic)

| Compd. No. | R | m.p. (°C.) | Appearance | Recrystalli-zing Solvent | Molecular Formula | Elementary Analysis (%) Up (Calcd.) Down (Found) | | | | NMR (DMSO-d6) δ |
|---|---|---|---|---|---|---|---|---|---|---|
| | | | | | | C | H | N | S | |
| Ic-53 | 2-Me-thiophene | 320-323(d) | Yellow | EtOH—CHCl3 | C16H11N3OS | 65.51 65.58 | 3.78 3.87 | 14.32 14.32 | 10.93 10.79 | 2.60 (3H,s), 7.13 (1H,d), 7.65~7.85 (2H,m), 8.05~8.30 (1H,m), 8.60~8.80 (2H,m), 9.35 (1H,s) |
| Ic-54 | 3-Me-thiophene | 306-308(d) | Yellow | EtOH—CHCl3 | C16H11N3OS | 65.51 65.46 | 3.78 3.96 | 14.32 14.24 | 10.93 10.96 | 2.37 (3H,s), 7.65~7.90 (3H,m), 8.10~8.30 (1H,m), 8.60~8.80 (2H,m), 9.40 (1H,s) |
| Ic-55 | 3-Me-thiophene | 291(d) | Yellow | EtOH—CHCl3 | C16H11N3OS | 65.51 65.19 | 3.78 3.89 | 14.32 14.03 | 10.93 10.85 | 2.70 (3H,s), 7.20 (1H,d), 7.65~7.90 (2H,m), 8.05~8.30 (1H,m), 8.07 (1H,d), 8.60~8.80 (1H,m), 9.37 (1H,s) |
| Ic-56 | furan | 305-307(d) | Yellow | EtOH—CHCl3 | C16H9N3O2 | 68.44 68.56 | 3.45 3.51 | 15.96 16.07 | | 6.83~6.97 (1H,m), 7.63~7.90 (2H,m), 8.10~8.30 (2H,m), 8.50 (1H,d), 8.60~8.77 (1H,m), 9.37 (1H,s) |
| Ic-57 | 2-Me-furan | 316-318(d) | Yellow | EtOH—CHCl3 | C16H11N3O2 | 69.31 69.31 | 4.00 3.94 | 15.15 15.16 | | 2.47 (3H,s), 6.57 (1H,d), 7.65~7.90 (2H,m), 8.10~8.30 (1H,m), 8.45 (1H,d), 8.60~8.80 (1H,m), 9.35 (1H,s) |
| Ic-58 | 3-Me-furan | 295-297(d) | Colorless | EtOH | C15H9N3O2 | 68.44 68.73 | 3.45 3.63 | 15.96 16.05 | | 7.23 (1H,d), 7.65~7.90 (2H,m), 7.97 (1H,m), 8.05~8.30 (1H,m), 8.60~8.85 (1H,m), 9.30 (1H,d), 9.37 (1H,s) |

TABLE 4-continued (Ic)

| Compd. No. | R | m.p. (°C.) | Appearance | Recrystallizing Solvent | Molecular Formula | Elementary Analysis (%) Up (Calcd.) Down (Found) C  H  N | NMR (DMSO-d6) δ |
|---|---|---|---|---|---|---|---|
| Ic-59 | 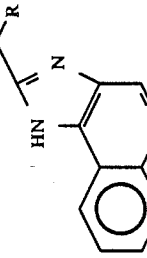 | 263-265(d) | Yellow | EtOH | C14H8N4O2 | 63.63  3.05  21.20<br>63.74  3.23  20.96 | 7.57 (1H,d), 7.70~7.90 (2H,m), 8.10~8.30 (1H,m), 8.60~8.80 (1H,m), 7.30 (1H,d), 7.40 (1H,s) |
| Ic-60 | 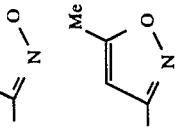 | 276-278(d) | Yellow | EtOH—CHCl3 | C15H10N4O2 | 64.74  3.62  20.13<br>64.98  3.78  19.97 | 2.59 (3H,s), 7.23 (1H,s), 7.60~7.90 (2H,m), 8.05~8.30 (1H,m), 8.55~8.75 (1H,m), 9.37 (1H,s) |
| Ic-61 | 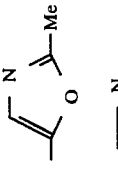 | 330(d) | Yellow | EtOH—CHCl3 | C15H10N4O2 | 64.74  3.62  20.13<br>64.65  3.60  19.97 | *Not measured, as it was difficult to dissolve the compound |
| Ic-62 |  | 291-293(d) | Light yellow | EtOH—CHCl3 | C15H10N4O2 | 64.74  3.62  20.13<br>65.05  3.75  19.79 | 2.53 (3H,s), 7.65~7.85 (2H,m), 8.05~8.25 (1H,m), 8.55~8.80 (1H,m), 9.31 (1H,s), 9.47 (1H,s) |
| Ic-63 | 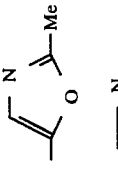 | 325(d) | Light yellow | MeOH—CHCl3 | C15H10N4OS | 61.21  3.42  19.04  S 10.89<br>61.29  3.62  18.71  S 10.69 | *Measuring solvent CDCl3—CD3OD, 2.85 (3H,s), 8.65~8.90 (2H,m), 8.10~8.30 (1H,m), 8.40~8.60 (1H,m), 9.30 (1H,s), 9.55 (1H,s) |

EXAMPLE 64

2-Benzoyl-8-fluoro-1H-imidazo[4,5-c]quinoline (I d-1)

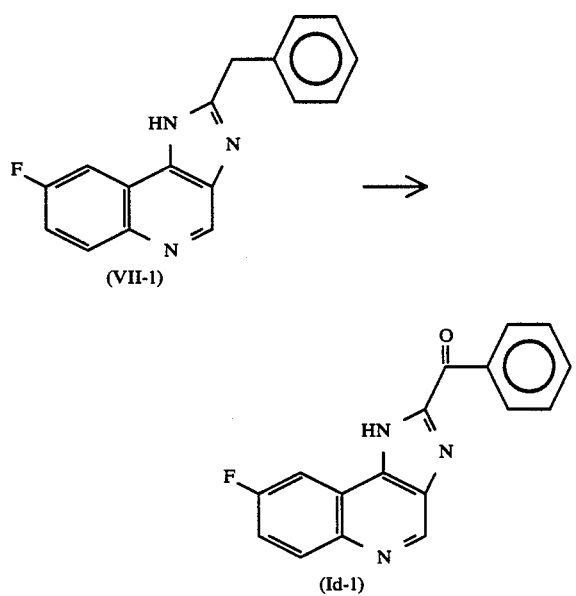

To a suspension of 830 mg of 2-benzyl-8-fluoro-1H-imidazo[4,5-c]-quinoline (VII-1) in 50 ml of dioxane heated to 80° C. was added 1.07 g of selenium dioxide. The reaction mixture was refluxed for 1.5 hours. The resulting precipitate was immediately removed by filtration and concentrated under reduced pressure, and the residue obtained was partitioned between ethyl acetate and saturated aqueous sodium hydrogencarbonate. The organic layer was washed with water and saturated brine, and dried. The ethyl acetate was removed and the residue was chromatographed on a column of silica gel for purification. After elution with chloroform-methanol (30:1 v/v), 820 mg (yield 94%) of the compound (I d-1) was obtained as crystals. This was recrystallized from ethanol-chloroform to give light yellow crystals melting at 255°~256° C.

Anal. Calcd. (%) for $C_{17}H_{10}N_3OF$ : C, 70.10; H, 3.46; N, 14.43; F, 6.52. Found (%): C, 70.22; H, 3.57; N, 14.43; F, 6.64.

NMR (DMSO-$d_6$)δ: 7.50~7.90 (4H, m), 8.07~8.47 (2H, m), 8.53~8.75 (2H, m), 9.31 (1H, s).

EXAMPLES 65~67

In the same manner as in Example 64, the objective compounds (I d) were obtained under the reaction conditions shown in Table 5. The physical properties of the compounds were shown in Tables 6-1 and 6-2.

TABLE 5

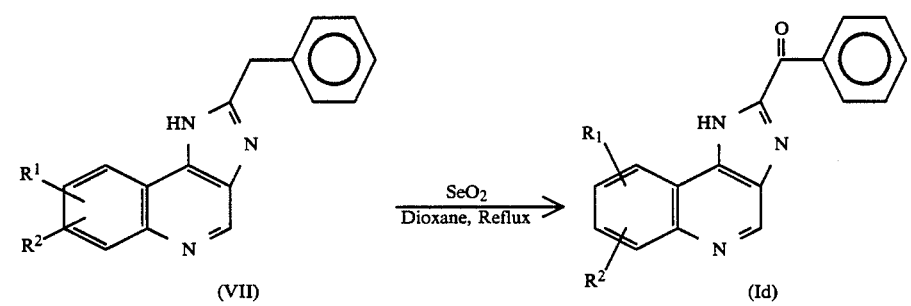

| Ex. No. | Compound (VII) R¹ | R² | Amount of (mg) | Selenium dioxide (mg) | Dioxane (ml) | Reflux Time (hr) | Compound (Id) Yield (mg) | (%) | Compd. No. |
|---|---|---|---|---|---|---|---|---|---|
| 65 | H | H | 300 | 420 | 20 | 1 | 285 | 90 | Id-2 |
| 66 | 7-F | H | 700 | 1000 | 40 | 2 | 270 | 37 | Id-3 |
| 67 | 7-OMe | H | 500 | 615 | 30 | 1 | 335 | 64 | Id-4 |

TABLE 6

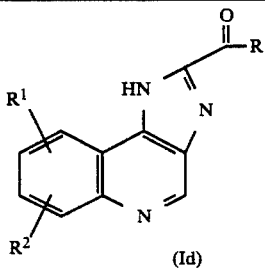
(Id)

| Compd. No. | R | R¹ | R² | m.p. (°C.) | Appearance | Solvent for Recrystalln. | Molecular Formula | Elementary Analysis (%) Up (Calcd.), Down (Found) | | | NMR (DMSO-d₆), δ |
|---|---|---|---|---|---|---|---|---|---|---|---|
| | | | | | | | | C | H | N | |
| Id-2 | –⟨O⟩ | H | H | 285–287 | Colorless | EtOH | $C_{17}H_{11}N_3O$ | 74.71<br>74.85 | 4.06<br>4.16 | 15.38<br>15.22 | 7.53~7.90 (5H,m),<br>8.17~8.27 (1H,m),<br>8.53~8.70 (3H,m),<br>9.37 (1H,s) |
| Id-3 | –⟨O⟩ | 7-F | H | 318–320(d) | Light yellow | EtOH—CHCl₃ | $C_{17}H_{10}N_3OF$ | 70.10<br>70.21 | 3.46<br>3.53 | 14.43 F 6.52<br>14.45 F 6.55 | 7.50~7.97 (5H,m),<br>8.53~8.85 (3H,m),<br>9.37 (1H,s) |
| Id-4 | –⟨O⟩ | 7-OMe | H | 322–324(d) | Colorless | EtOH—CHCl₃ | $C_{18}H_{13}N_3O_2$ | 71.28<br>71.36 | 4.32<br>4.25 | 13.85<br>13.61 | 3.95 (3H,s),<br>7.30~7.90 (5H,m),<br>8.47~8.80 (3H,m),<br>9.33 (1H,s) |

EXAMPLE 68

2-Ethoxycarbonyl-1H-imidazo[4,5-c]quinoline (I c-64)

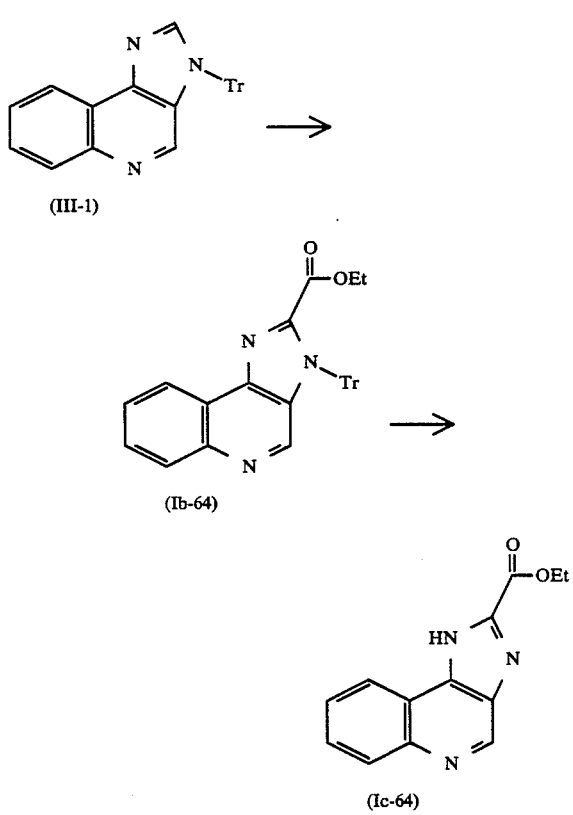

To a solution prepared in the same manner as in Example 1 from 410 mg of the compound (III-1) in 5 ml of THF and a mixture of 1 ml of 1.6M solution of n-butyl lithium in hexane-5 ml of THF was added 350 mg of ethyl chloroformate. The reaction mixture was warmed to room temperature and concentrated under reduced pressure. The residue was partitioned between ethyl acetate and saturated aqueous sodium hydrogencarbonate. The organic layer was washed with water and saturated brine, and dried. After evaporating the ethyl acetate, the residue was crystallized from n-hexane to give 455 mg of the compound (I b-64) as crude crystals. The compound (I b-64) was dealkylated by mixing with 4 ml of trifluoroacetic acid. After treatment in the same manner as in Example 1, the crude product was chromatographed on a column of silica gel for purification. After elution with chloroform-methanol (10:1 v/v) and evaporation of the fraction obtained, the residue was crystallized from n-hexane to give 200 mg (yield: 83%) of the titled compound (I c-64). This was recrytallized from ethyl acetate to give colorless crystals melting at 198°~200° C.

Anal. Calcd. (%) for $C_{13}H_{11}N_3O_2$: C, 64.72; H, 4.60; N, 17.42. Found (%): C, 64.74; H, 4.58; N, 17.43.

NMR (DMSO-d₆)δ: 1.42 (3H, t), 4.50 (2H, q), 7.60~7.90 (2H, m), 8.05~8.30 (1H, m), 8.55~8.75 (1H, m), 9.33 (1H, s).

EXAMPLE 69

2-Isopropyloxycarbonyl-1H-imidazo[4,5-c]quinoline (I c-65)

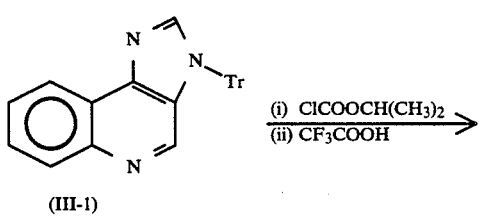

(III-1)

(i) ClCOOCH(CH3)2
(ii) CF3COOH

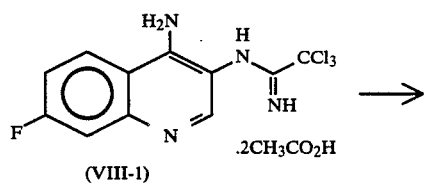

(Ic-65)

In the same manner as in Example 68, isopropyl chloroformate was allowed to react with III-1 to give the titled compound (I c-65) in 50 % yield. This was crystallized from ethyl acetate to give colorless crystals melting at 245°~247° C.

Anal. Calcd. (%) for $C_{14}H_{13}N_3O_2$: C, 65.87; H, 5.13; N, 16.46. Found (%): C, 65.80; H, 5.24; N, 16.42.

NMR (DMSO-d6)δ: 1.43 (6H, d), 5.30 (1H, septet), 7.60~7.85 (2H, m), 8.05~8.25 (1H, m), 8.50~8.70 (1H, m), 9.30 (1H, s).

EXAMPLE 70

2-Ethoxycarbonyl-7-fluoro-1H-imidazo[4,5-c]quinoline (I e-1)

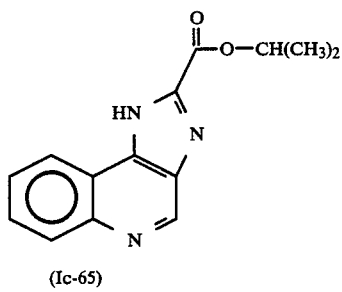

(VIII-1)

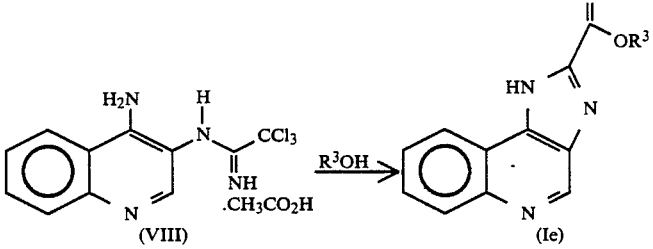

(Ie-1)

A solution of 1.15 g of 4-amino-7-fluoro-3-(trichloroacetimidoylamino)quinoline diacetate (VIII-1) in 120 ml of ethanol was heated under reflux for two hours. The reaction mixture was concentrated under reduced pressure, and the residue was added to ice-water. After being basified with 2N aqueous ammonia, the mixture was extracted with chloroform. The extract was washed with water and brine, and then dried. The chloroform was removed by evaporation. The residue was chromatographed on a column of silica gel with chloroform-methanol (100:1 v/v), whereby 395 mg (yield: 59%) of the titled compound (I e-1) was obtained as crystals. These were recrystallized from chloroform-ethanol to give colorless crystals melting at 238°~240° C. (d).

Anal. Calcd. (%) for $C_{13}H_{10}N_3O_2F$: C, 60.23; H, 3.89; N, 16.21; F, 7.33. Found (%): C, 60.16; H, 4.03; N, 16.29; F, 7.41.

NMR (DMSO-d6)δ: 1.41 (3H, t), 4.49 (2H, q), 7.50~8.10 (2H, m), 8.60~8.80 (1H, m), 9.33 (1H, s).

EXAMPLES 71~72

In the same manner as in Example 70, the objective compounds (Ie) were obtained under reaction conditions shown in Table 7. The physical properties of the compounds were shown in Tables 8-1 and 8-2.

TABLE 7

| Ex. No. | R³ | Amount of VIII (mg) | R³OH (ml) | Reaction Temp. (°C.) | Reaction Time (hr) | Compound (Ie) Yield (mg) | (%) | Compd. No. |
|---|---|---|---|---|---|---|---|---|
| 71 | —CH3 | 800 | 20 | Reflux | 16 | 234 | 47 | Ie-2 |
| 72 | —(CH2)2CH3 | 182 | 20 | 80 | 4 | 68 | 53 | Ie-3 |

TABLE 8

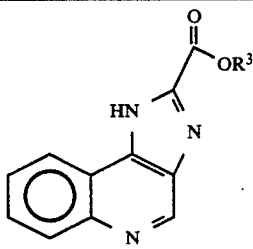

(Ie)

| Compd. No. | R³ | m.p. (°C.) | appearance | Solvent for recrystalln. | Molecular Formula | Elementary Analysis (%) Up (Calcd.), Down (Found) C | H | N | NMR (DMSO-d₆), δ |
|---|---|---|---|---|---|---|---|---|---|
| Ie-2 | —CH₃ | 218–219(d) | Colorless | EtOH—CHCl₃ | C₁₂H₉N₃O₂ | 63.42 / 63.14 | 3.99 / 3.99 | 18.49 / 18.21 | 4.00(3H, s), 7.60~8.70 (4H, m), 9.27(1H, s) |
| Ie-3 | —(CH₂)₂CH₃ | 214–217 | Colorless | EtOH—CHCl₃ | C₁₄H₁₃N₃O₂ | 65.87 / 65.43 | 5.13 / 5.21 | 16.46 / 16.50 | 1.00(3H, t), 1.80(2H, m), 4.37(2H, t), 7.60~8.80 (4H, m), 9.27(1H, s) |

EXAMPLE 73

2-Methylcarbamoyl-1H-imidazo[4,5-c]quinoline (Ic-66)

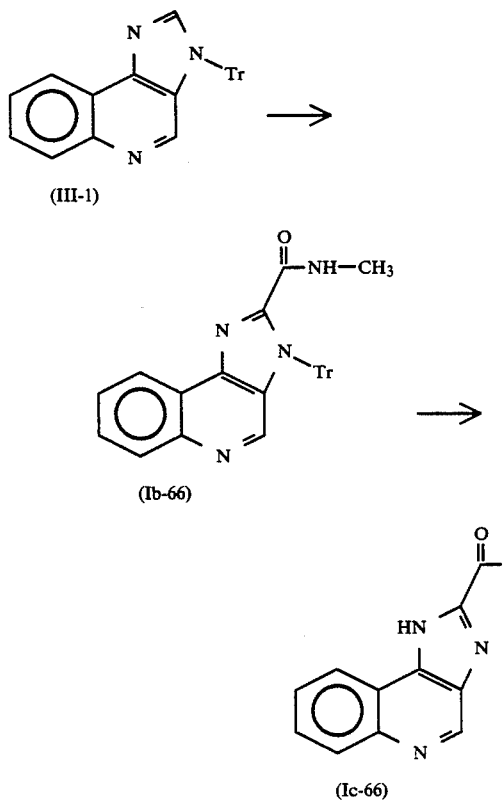

To a solution prepared in the same manner as in Example 1 from 1.23 g of the compound (III-1) in 30 ml of THF and a mixture of 4 ml of 1.6M solution of n-butyl lithium in hexane-4 ml of THF was added 770 mg of methyl isocyanate. The reaction mixture was gradually warmed to room temperature and concentrated under reduced pressure. Water was added to the residue, and the product was extracted with ethyl acetate. The extract was washed with water and brine, and then dried. The ethyl acetate was removed and the residue was crystallized from ether to give 990 mg of the compound (Ib-66) as crude crystals. The compound (Ib-66) was dealkylated by mixing with 4 ml of trifluoroacetic acid and stirred for 30 min. at room temperature. The reaction mixture was concentrated under reduced pressure, and the residue was neutralized with saturated aqueous sodium hydrogencarbonate. The crystals precipitated were collected by filtration, washed with water and ethanol, and then dried to give 410 mg (yield: 61%) of the titled compound (Ic-66). The compound (Ic-66) was recrystallized from ethanol-chloroform to give colorless crystals, m.p. at 322° C. (s).

Anal Calcd. (%) for C₁₂H₁₀N₄C: C, 63.71; H, 4.46; N, 24.76. Found (%): C, 63.60; H, 4.60; N, 24.48.

NMR (DMSO-d₆-CD₃OD)δ: 3.93 (3H, s), 7.57~7.90 (2H, m), 8.07~8.30 (1H, m), 8.55~8.80 (1H, m), 9.27 (1H, s).

EXAMPLES 74~76

In the same manner as in Example 73, the objective compounds (Ic) were obtained under the reaction conditions shown in Table 9. The physical properties of the compounds were shown in Tables 10-1 and 10-2.

TABLE 9

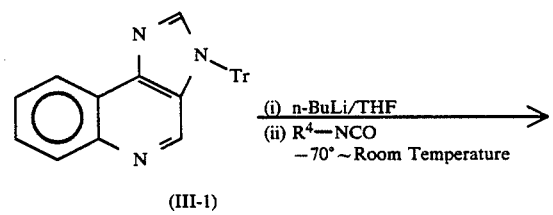

TABLE 9-continued

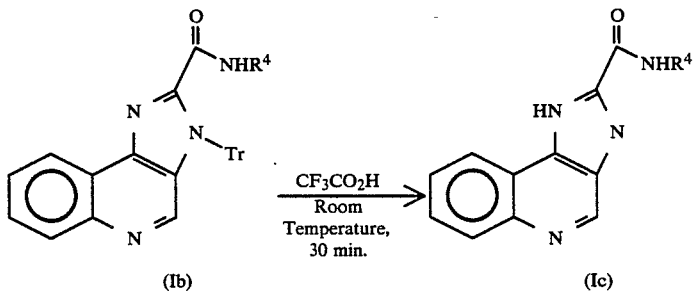

| Ex. No. | R⁴ | 1st Step | | | | 2nd Step | Compound (Ic) | | |
|---|---|---|---|---|---|---|---|---|---|
| | | Amount of III-1 (g) | Solvent THF (ml) | n-BuLi—THF (ml) | R⁴NCO (g) | CF₃CO₂H (ml) | Yield (mg) | (%) | Compd. No. |
| 74 | —C₂H₅ | 1.23 | 25 | 2.5 | 2 | 0.63 | 4 | 300 | 42 | Ic-67 |
| 75 | —(CH₂)₂CH₃ | 1.23 | 25 | 2.5 | 2 | 0.68 | 3 | 260 | 34 | Ic-68 |
| 76 | —CH(CH₃)₂ | 1.23 | 25 | 2.5 | 2 | 0.69 | 4 | 540 | 71 | Ic-69 |

TABLE 10

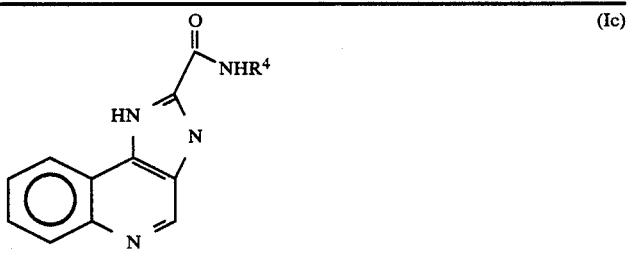

| Compd. No. | R⁴ | m.p. (°C.) | Appearance | Solvent for Recrystalln. | Molecular Formula | Elementary Analysis (%) Up (Calcd.), Down (Found) | | |
|---|---|---|---|---|---|---|---|---|
| | | | | | | C | H | N |
| Ic-67 | —C₂H₅ | 296–297 | Colorless | EtOH—CHCl₃ | C₁₃H₁₂N₄O | 64.99 | 5.03 | 23.32 |
| | | | | | | 64.92 | 5.23 | 23.19 |
| Ic-68 | —(CH₂)₂CH₃ | 253–254 | Colorless | EtOH | C₁₄H₁₄N₄O | 66.13 | 5.55 | 22.03 |
| | | | | | | 66.12 | 5.47 | 21.92 |
| Ic-69 | —CH(CH₃)₂ | 263–264 | Colorless | EtOH | C₁₄H₁₄N₄O | 66.13 | 5.55 | 22.03 |
| | | | | | | 66.08 | 5.57 | 21.96 |

| Compound No. | NMR (DMSO-d₆) δ |
|---|---|
| Ic-67 | 1.17 (3H,t), 3.20~3.57 (2H,m), 7.60~7.90 (2H,m), 8.05~8.30 (1H,m), 8.55~8.80 (1H,m), 9.13 (1H,t), 9.37 (1H,s) |
| Ic-68 | 0.93 (3H,t), 1.65 (2H,t,q), 3.35 (2H,d,t), 7.60~7.90 (2H, m), 8.10~8.30 (1H,m), 8.55~8.80 (1H,m), 9.10 (1H,t), 9.30 (1H,s) |
| Ic-69 | 1.27 (6H,d), 4.05~4.45 (1H,m), 7.65~7.90 (2H,m), 8.10~8.30 (1H,m), 8.10~8.30 (1H,m), 8.55~8.75 (1H,m), 8.87 (1H,d), 9.30 (1H,s) |

EXAMPLE 77

2-Carbamoyl-1H-imidazo[4,5-c]quinoline (Ig-1)

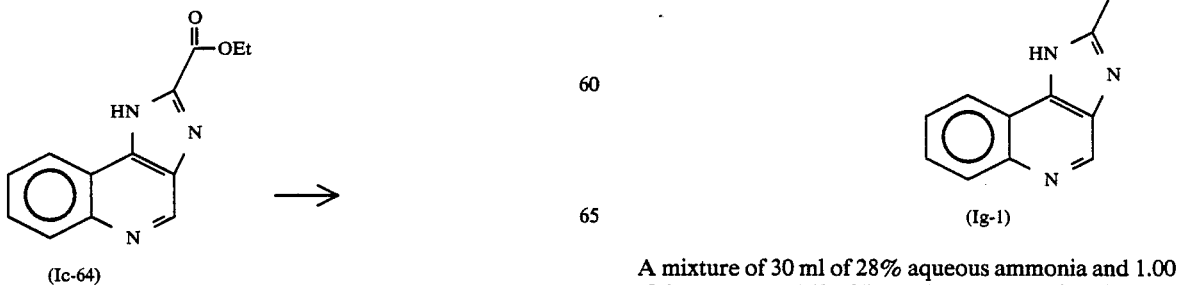

A mixture of 30 ml of 28% aqueous ammonia and 1.00 g of the compound (Ic-64) was heated at 100° C. for two hours in a sealed tube. The reaction mixture was concentrated to 20 ml of the volume, and the resulting crystals were washed successively with water, ethanol, and n-hexane, whereby 688 mg (yield: 74%) of the titled compound (Ig-1) was obtained. This was recrystallized from methanol-chloroform to give colorless crystals, m.p. 326°~328° C.

Anal. Calcd. (%) for $C_{11}H_8N_4O \cdot \frac{3}{8}H_2O$: C, 58.92; H, 4.20; N, 24.99. Found (%): C, 58.95; H, 4.02; N, 24.95.

Mass spectrum: m/z, 212 (M+).

NMR (DMSO-$d_6$-CD$_3$OD)δ: 7.55~7.85 (2H, m), 8.05~8.25 (1H, m), 8.55~8.75 (1H, m), 9.23 (1H, s).

EXAMPLE 78

2-Diethylcarbamoyl-1H-imidazo[4,5-c]quinoline (Ig-2)

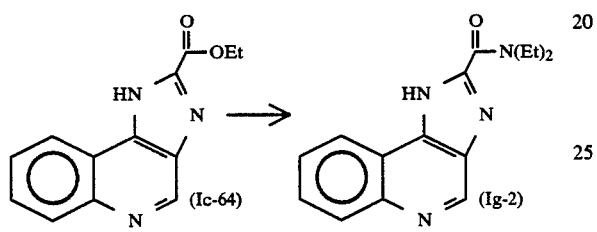

To a solution of 560 mg of the compound (Ic-64) in 10 ml of ethanol was added 4.8 ml of 1N aqueous sodium hydroxide, and the mixture was refluxed for one hour. The reaction mixture was concentrated under reduced pressure. The residue was dissolved in 10 ml of water, and acidified with 5.2 ml of 1N aqueous hydrochloric acid. The precipitated crystals were collected by filtration, washed with water and dried, whereby 440 mg of carboxylic acid were obtained as crude crystals. These were suspended in 8 ml of thionyl chloride, and the suspension was refluxed for 30 min. The excess thionyl chloride was evaporated under reduced pressure, and 10 ml of toluene was added to the residue. After stirring the mixture, the toluene was evaporated under reduced pressure. To a suspension of the resulting residue in 10 ml of dichloromethane was added 2 ml of diethylamine at room temperature, and the mixture was stirred vigorously for 30 min. The reaction mixture was concentrated under reduced pressure, and the residue was partitioned between ethyl acetate and water. The organic layer was washed with water and brine, and then dried. The ethyl acetate was removed and the residue was chromatographed on a column of silica gel for purification. The fraction eluted with chloroform-methanol (10:1 v/v) was concentrated and the residue was crystallized from n-hexane to give 110 mg (yield: 10%) of the titled compound (Ig-2). This was recrystallized from ethyl acetate-n-hexane to give colorless crystals melting at 179°~181° C.

Anal. Calcd. (%) for $C_{15}H_{16}N_4O$: C, 67.15; H, 6.01; N, 20.88. Found (%): C, 67.05; H, 6.00; N, 20.52.

NMR (DMSO-$d_6$), δ: 1.23 (3H, t), 1.31 (3H, t), 3.57 (2H, q), 4.13 (2H, q), 7.60~7.90 (2H, m), 8.03~8.30 (1H, m), 8.53~8.80 (1H, m), 9.29 (1H, s).

EXAMPLE 79

2-Dimethylcarbamoyl-1H-imidazo[4,5-c]quinoline (Ic-70)

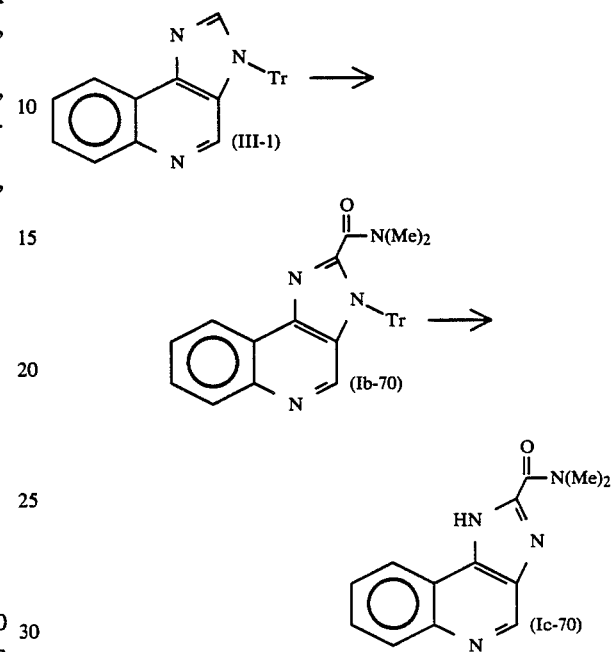

In the same manner as in Ex. 1, to a solution containing 1.23 g of the compound (III-1) in 25 ml of THF and a mixture of 2.5 ml of 1.6M solution of n-butyl lithium in hexane-2 ml of THF was added 930 mg of dimethylcarbamoyl chloride, and the usual workup gave 610 mg of the compound (Ib-70) as crude crystals. The compound (Ib-70) was dealkylated by mixing with 3 ml of trifluoroacetic acid. The crude crystals were chromatographed on a column of silica gel with chloroform-methanol (30:1 v/v), whereby 280 mg (yield: 30%) of the titled compound (Ic-70) was obtained. This was recrystallized from ethanol to give colorless crystals, m.p. 284°~286° C.

Anal. Calcd. (%) for $C_{13}H_{12}N_4O$: C, 64.99; H, 5.03; N, 23.32. Found (%): C, 65.17; H, 5.15; N, 23.25.

NMR (DMSO-$d_6$), δ: 3.15 (3H, s), 3.67 (3H, s), 7.60~7.90 (2H, m), 8.05~8.25 (1H, m), 8.55~8.75 (1H, m), 9.27 (1H, s).

EXAMPLE 80

2-Carboxy-1H-imidazo[4,5-c]quinoline (If-1)

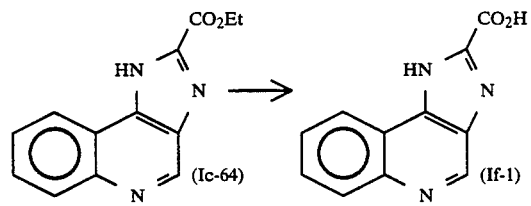

To a solution of 240 mg of the compound (Ic-64) in 4 ml of ethanol was added 2 ml of 1N aqueous sodium hydroxide, and the mixture was refluxed for one hour. The reaction mixture was concentrated under reduced pressure. The residue was dissolved in 5 ml of water, and acidified with 2.2 ml of 1N aqueous hydrochloric acid. The precipitated crystals were collected by filtration, washed with water, and dried at room temperature under reduced pressure to give 200 mg (yield: 94%) of the titled compound (If-1).

Melting point: 165°~167° C. (d).

Anal. Calcd. (%) for $C_{11}H_7N_3O_2$: C, 61.97; H, 3.31; N, 19.71. Found (%): C, 61.88; H, 3.51; N, 19.65.

NMR (DMSO-$d_6$)δ: 7.55~7.95 (2H, m), 8.05~8.35 (1H, m), 8.50~8.85 (1H, m), 9.30 (1H, s).

EXAMPLE 81

2-Cyclopropylcarbonyl-1-methyl-1H-imidazo[4,5-c]quinoline (Ia-1)

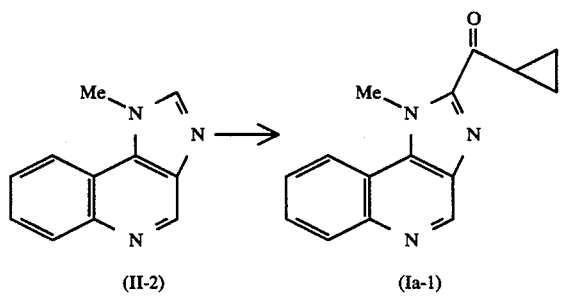

In the same manner as in Ex. 1, to a solution containing 550 mg of 1-methyl-1H-imidazo[4,5-c]quinoline (II-2) in 25 ml of THF and a mixture of 2.2 ml of 1.6M solution of n-butyl lithium in hexane-2 ml of THF was added 0.75 g of cyclopropanecarbonyl chloride. The reaction mixture was gradually warmed to room temperature and concentrated under reduced pressure. The residue was partitioned between ethyl acetate and aqueous ammonia. The organic layer was washed with water and brine, and then dried. The ethyl acetate was removed by evaporation, and the residue was chromatographed on a column of silica gel for purification. The fraction eluted with ethyl acetate was concentrated and the residue was crystallized from n-hexane to give 275 mg (yield: 36%) of the titled compound (Ia-1). This was recrystallized from ethyl acetate n-hexane to give colorless crystals melting at 156°~158° C.

Anal. Calcd. (%) for $C_{16}H_{13}N_3O$: C, 71.70; H, 5.21; N, 16.72. Found (%): C, 71.62; H, 5.13; N, 16.64.

NMR (DMSO-$d_6$)δ: 1.05~1.45 (4H, m), 3.45~3.75 (1H, m), 4.63 (3H, s), 7.55~7.85 (2H, m), 8.35~8.50 (2H, m), 9.40 (1H, s).

EXAMPLE 82–83

In the same manner as in Ex. 81, the objective compounds (Ia) were obtained under the reaction conditions shown in Table 11. The physical properties of the compounds were shown in Tables 12-1 and 12-2.

TABLE 11

| Ex. No. | Amount of Compd. II-2 (g) | Solvent THF (ml) | RCOCl R | RCOCl (g) | n-BuLi—THF (ml) | n-BuLi—THF (ml) | Compound (Ia) Yield (mg) | Compound (Ia) Yield (%) | Compd. No. |
|---|---|---|---|---|---|---|---|---|---|
| 82 | 0.55 | 25 | —C₆H₅ | 1.15 | 2.5 | 2 | 290 | 34 | Ia-2 |
| 83 | 0.55 | 25 | —OEt | 0.80 | 2.5 | 2 | 290 | 38 | Ia-3 |

TABLE 12

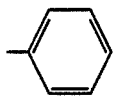

(Ia)

| Compd. No. | R | m.p. (°C.) | Appearance | Solvent for Recrystalln. | Molecular Formula | Elementary Analysis (%) Up (Calcd.) Down (Found) | | |
|---|---|---|---|---|---|---|---|---|
| | | | | | | C | H | N |
| Ia-2 | (phenyl) | 195–197 | Colorless | AcOEt | $C_{18}H_{13}N_3O$ | 75.25<br>75.55 | 4.56<br>4.56 | 14.62<br>14.66 |
| Ia-3 | —OEt | 149–151 | Colorless | AcOEt-n-Hexane | $C_{14}H_{13}N_3O_2$ | 65.87<br>65.87 | 5.13<br>5.10 | 16.46<br>16.42 |

| Compound No. | NMR (CDCl₃) δ |
|---|---|
| Ia-2 | 4.60 (3H,s), 7.40~7.85 (5H,m), 8.20~8.50 (4H,m), 9.40 (1H,s) |
| Ia-3 | 1.50 (3H,t), 4.55 (2H,q), 4.63 (3H,s), 7.55~7.85 (2H,m), 8.20~8.45 (2H,m), 9.40 (1H,s) |

EXAMPLES 84–90

In the same manner as in Examples 1, 2, 35, or 36, the objective compounds (Ic) were obtained under the reaction conditions shown in Table 13. The properties of the compounds were shown in Tables 14-1 and 14-2.

TABLE 13

| | | Amount of Compd. (III) | | | Solvent THF | n-BuLi—THF | | RCO-X | | 2nd Step CF₃CO₂H | Compound (Ic) Yield | | |
|---|---|---|---|---|---|---|---|---|---|---|---|---|---|
| Ex No. | R | R¹ | R² | (g) | (ml) | (ml) | (ml) | X | (g) | (ml) | (mg) | (%) | Compd. No. |
| 84 | (3-methyl-5-methylisoxazolyl) | 8-F | H | 1.28 | 90 | 2 | 2 | Cl | 1.10 | 3 | 50 | 6 | Ic-71 |
| 85 | (3-furyl) | 8-F | H | 1.28 | 90 | 2 | 2 | Cl | 1.05 | 4 | 470 | 56 | Ic-72 |
| 86 | (2,5-dimethylthienyl) | 7-F | H | 1.29 | 80 | 2.2 | 2 | OMe | 1.1 | 4 | 270 | 28 | Ic-73 |

TABLE 13-continued

[Reaction scheme: Compound (III) → (1) n-BuLi/THF, -70°C, 30 min. (2) RCO-X, -70°C ~ Room Temperature → Compound (Ib) → CF₃CO₂H, Room Temperature, 30 min. → Compound (Ic)]

1st Step

| Ex No. | R | R¹ | R² | Amount of Compd. (III) (g) | Solvent THF (ml) | n-BuLi—THF (ml) | (ml) | RCO-X X | (g) | 2nd Step CF₃CO₂H (ml) | Compound (Ic) Yield (mg) | (%) | Compd. No. |
|---|---|---|---|---|---|---|---|---|---|---|---|---|---|
| 87 | [3-methyl-5-phenylisoxazole] | H | H | 1.23 | 25 | 2.5 | 2 | Cl | 1.70 | 4 | 460 | 45 | Ic-74 |
| 88 | —(CH₂)₂—Ph | 7-F | H | 1.29 | 80 | 2.2 | 2 | Cl | 1.36 | 3 | 155 | 16 | Ic-75 |
| 89 | [cyclopropyl] | 8-OMe | H | 1.32 | 30 | 2.5 | 2 | Cl | 1.04 | 4 | 310 | 39 | Ic-76 |
| 90 | —CH(CH₃)₂ | 8-OMe | H | 1.32 | 30 | 2.5 | 2 | —OCOCH(CH₃)₂ | 1.33 | 4 | 630 | 78 | Ic-77 |

TABLE 14

[Structure of compound (Ic)]

| Compd. No. | R¹ | R² | R | m.p. (°C.) | Appearance | Recrystallizing Solvent | Molecular Formula | Elementary Analysis (%) Up (Calcd.), Down (Found) C | H | N |
|---|---|---|---|---|---|---|---|---|---|---|
| Ic-71 | 8-F | H | [3-methyl-5-methylisoxazole] | 275–277 (d) | Colorless | EtOH | C₁₆H₉N₄O₂F | 60.81 3.06 | 18.91 F, 6.41 | |
| | | | | | | | | 61.02 3.28 | 18.81 F, 6.47 | |
| Ic-72 | 8-F | H | [3-methylfuran] | 310–312 | Light yellow | EtOH—CHCl₃ | C₁₆H₈N₃O₂F | 64.06 2.87 | 14.94 F, 6.75 | |
| | | | | | | | | 64.03 2.93 | 14.92 F, 6.73 | |
| Ic-73 | 7-F | H | [2,5-dimethylthiophene] | >310 | Light yellow | DMF | C₁₆H₁₉N₃O₂FS | 61.73 3.24 | 13.50 F, 6.10 S, 10.30 | |
| | | | | | | | | 61.56 3.40 | 13.44 F, 6.10 S, 10.30 | |
| Ic-74 | H | H | [3-methyl-5-phenylisoxazole] | 295–297 (d) | Light yellow | EtOH—CHCl₃ | C₂₀H₁₂N₄O₂ | 70.58 3.55 | 16.46 | |
| | | | | | | | | 70.78 3.69 | 16.26 | |
| Ic-75 | 7-F | H | —(CH₂)₂—Ph | 274–276 | Colorless | EtOH—CHCl₃ | C₁₉H₁₄N₃OF | 71.46 4.42 | 13.16 F, 5.95 | |
| | | | | | | | | 71.72 4.58 | 13.31 F, 6.15 | |

TABLE 14-continued (Ic)

| | | | | | | | | | |
|---|---|---|---|---|---|---|---|---|---|
| Ic-76 | 8-OMe | H | ◁ | 185–187 (d) | Colorless | EtOH | $C_{16}H_{13}N_3O_2$ | 67.41 4.90 67.16 4.79 | 15.72 15.58 |
| Ic-77 | 8-OMe | H | —CH(CH$_3$)$_2$ | 188–190 | Colorless | AcOEt | $C_{15}H_{15}N_3O_2$ | 66.90 5.61 66.89 5.66 | 15.60 15.53 |

| Compd. No | NMR (DMSO-d$_6$) δ |
|---|---|
| Ic-71 | 2.63(3H, s), 7.23(1H, s), 7.50~7.75(1H, m), 8.10~8.40(2H, m), 9.30(1H, s) |
| Ic-72 | 7.17(1H, d), 7.47~7.77(1H, m), 7.93(1H, d), 8.05~8.45 (2H, m), 9.37(2H, s) |
| Ic-73 | 2.61 (3H, s), 7.13 (1H, d), 7.55~7.97 (2H, m), 8.65~8.85 (2H, m), 9.30 (1H, s) |
| Ic-74 | Measuring Solvent CDCl$_3$-CD$_3$OD 7.45~8.05(8H, m), 8.10~8.30(1H, m), 8.50~8.70(1H, m) 9.40(1H, s) |
| Ic-75 | 3.07(2H, t), 3.60(2H, t), 7.10~7.45(5H, m), 7.50~7.95 (2H, m), 8.55~8.80(1H, m), 9.33(1H, s) |
| Ic-76 | 1.35(4H, d), 3.37(1H, quintet), 3.97(3H, s) 7.37(1H, d, d), 7.97-8.20(2H, m) 9.27(1H, s) |
| Ic-77 | 1.30(6H, d), 3.90(1H, septet), 3.97(3H, s), 7.37 (1H, d, ), 8.00~8.15(2H, m), 9.15(1H, s) |

REFERENTIAL EXAMPLE 1

1H-Imidazo[4,5-c]quinoline (II-1)

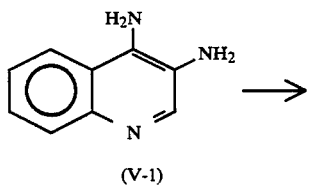

(V-1)

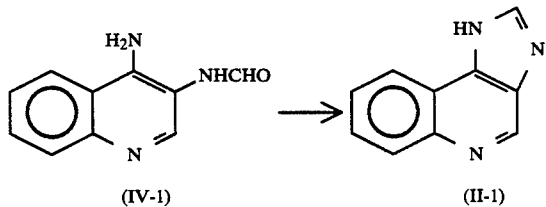

(IV-1) (II-1)

A solution of 5.0 g of 3,4-diaminoquinoline (V-1) in 15 ml of formic acid was refluxed for one hour. The reaction solution was concentrated under reduced pressure, and the residue obtained was neutralized with saturated aqueous sodium hydrogencarbonate. This was allowed to stand overnight. The precipitated crystals were collected by filtration, washed with water, and dried to give 5.6 g of crystals (IV-1). The crystals were suspended in 120 ml of diglyme, and the suspension was refluxed for 1,5 hours. The reaction mixture was cooled down and the precipitated crystals were collected by filtration, and washed with ethyl acetate and n-hexane, successively, to give 5.1 g (yield: 96%) of the titled compound (II-1). This was recrystallized from ethanol to give colorless crystals melting at 294°~296° C.

Anal. Calcd. (%) for $C_{10}H_7N_3$: C, 70.99; H, 4.17; N, 24.84. Found (%): C, 71.12; H, 4.27; N, 24.76.

NMR (DMSO-d$_6$)δ: 7.50~7.85 (2H, m), 8.03~8.27 (1H, m), 8.33~8.57 (1H, m), 8.53 (1H, s), 9.27 (1H, s).

REFERENTIAL EXAMPLES 2–6

In the same manner as in Referential Example 1, the compounds (IV) were obtained under the reaction conditions shown in Table 15. The physical properties of the compounds (II) were shown in Tables 14-1 and 14-2.

TABLE 15

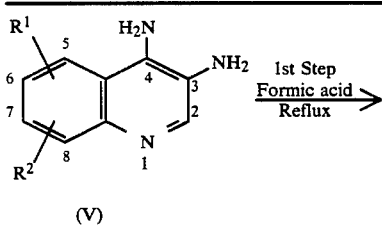

(V)

TABLE 15-continued (IV) → (II) 2nd Step Diglyme Reflux

| Ref. Ex. No. | Amount of Compound (V) | | | 1st Step Formic acid (ml) | Reflux Time (hr) | 2nd Step Diglyme (ml) | Reflux Time (hr) | Compound (II) | | |
|---|---|---|---|---|---|---|---|---|---|---|
| | $R^1$ | $R^2$ | (g) | | | | | Yield (g) | (%) | Compd. No. |
| 2 | 7-OMe | H | 4.55 | 14 | 1 | 150 | 4 | 4.34 | 90 | II-2 |
| 3 | 6-F | H | 4.00 | 12 | 1 | 90 | 2 | 3.71 | 88 | II-3 |
| 4 | 7-F | H | 5.00 | 12 | 1.5 | 120 | 1.5 | 4.97 | 94 | II-4 |
| 5 | 6-Me | H | 1.90 | 6 | 1 | 70 | 1.5 | 1.30 | 65 | II-5 |
| 6 | 6-OMe | H | 2.54 | 8 | 1 | 100 | 3.5 | 2.34 | 88 | II-6 |

TABLE 16

(II)

| Compd. No. | $R^1$ | $R^2$ | m.p. (°C.) | Appearance | Solvent for Recrystalln. | Molecular Formula | Elementary Analysis (%) Up (Calcd.) Down (Found) | | |
|---|---|---|---|---|---|---|---|---|---|
| | | | | | | | C | H | N |
| II-2 | 7-OMe | H | 290–292(d) | Colorless | EtOH | $C_{11}H_9N_3O$ | 66.32 66.16 | 4.55 4.76 | 21.09 20.81 |
| II-3 | 8-F | H | 325–327(d) | Colorless | MeOH—CHCl$_3$ | $C_{10}H_8N_3F$ | 64.16 64.56 3.48 | 3.23 | 22.44 22.43 |
| II-4 | 7-F | H | 316–318(d) | Colorless | MeOH—CHCl$_3$ | $C_{10}H_8N_3F$ | 64.16 64.36 3.53 | 3.23 | 22.44 22.41 |
| II-5 | 8-Me | H | 319–321(d) | Colorless | EtOH | $C_{11}H_9N_3$ | 72.11 72.15 | 4.95 5.10 | 22.34 22.71 |
| II-6 | 8-OMe | H | 280–282 | Colorless | EtOH | $C_{11}H_9N_3O$ | 66.32 66.36 | 4.55 4.74 | 21.09 21.01 |

| Compound No. | NMR (DMSO-$d_6$) δ |
|---|---|
| II-2 | 3.93(3H, s), 7.35(1H, d, d), 7.55(1H, d), 8.33(1H, d), 8.43(1H, s), 9.17(1H, s) |
| II-3 | 7.42~7.66(1H, m), 8.04~8.30(2H, m), 8.53(1H, s), 9.22(1H, s) |
| II-4 | 7.48~7.93(2H, m), 8.40~8.57(1H, m), 8.53(1H, s), 9.27(1H, s) |
| II-5 | 2.57(3H, s), 7.49(1H, d, d), 8.03(1H, d), 8.27(1H, d), 8.47(1H, s), 8.17(1H, s) |
| II-6 | 3.97(3H, s), 7.30(1H, d, d), 7.83(1H, d), 8.05(1H, d), 8.48(1H, s), 9.10(1H, s) |

REFERENTIAL EXAMPLE 7

3-Trityl-3H-imidazo[4,5-c]quinoline (III-1)

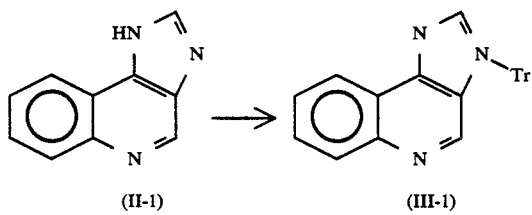

(II-1) → (III-1)

To a suspension of 5.2 g of 1H-imidazo[4,5-c]quinoline (II-1) in 180 ml of MeCN were added 10.3 g of trityl chloride and 4.2 g of triethylamine, and the mixture was stirred at room temperature for 8 hours. The reaction mixture was concentrated under reduced pressure, and the residue was partitioned between ethyl acetate and saturated aqueous sodium hydrogencarbonate. The organic layer was washed with water and brine, and then dried. The ethyl acetate was removed and the residue was chromatographed on a column of silica gel with ethyl acetate-n-hexane (1:1 v/v). Crystallization of the resulting oily substance from n-hexane gave 12.4 g (yield: 98%) of the titled compound (III-1). This was recrystallized from ethyl acetate-n-hexane to give colorless crystals melting at 190°~192° C.

Anal. Calcd. (%) for $C_{29}H_{21}N_3$: C, 84.64; H, 5.14; N, 10.21. Found (%): C, 84.58; H, 5.23; N, 10.14.

NMR (CDCl$_3$), δ: 7.10~7.50 (15H, m), 7.53~7.77 (2H, m), 8.07 (1H, s), 8.10 (1H, s), 8.00~8.20 (1H, m), 8.53~8.73 (1H, m).

REFERENTIAL EXAMPLES 8-12

In the same manner as in Ref. Ex. 7, the compounds (III) were obtained under the reaction conditions shown in Table 17. The physical properties of the compounds were shown in Tables 18-1 and 18-2.

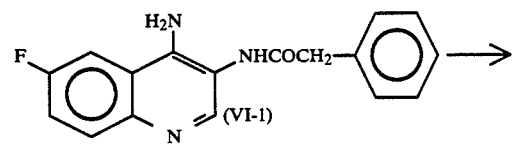

TABLE 17

| Ref. Ex. No. | Amount of Compound (II) | | TrCl (g) | Et$_3$N (g) | MeCN (ml) | Reaction Time (hr) | Compound (III) | | |
|---|---|---|---|---|---|---|---|---|---|
| | R$^1$ | R$^2$ | (g) | | | | Yield (g) | (%) | Compd. No. |
| 8 | 7-OMe | H | 4.18 | 7.10 | 3.00 | 75 | 8 | 8.60 | 93 | III-2 |
| 9 | 8-F | H | 3.35 | 5.99 | 2.35 | 130 | 15 | 6.81 | 88 | III-3 |
| 10 | 7-F | H | 4.50 | 8.05 | 3.16 | 160 | 24 | 9.01 | 88 | III-4 |
| 11 | 8-Me | H | 1.24 | 2.30 | 0.95 | 40 | 12 | 2.68 | 97 | III-5 |
| 12 | 8-OMe | H | 2.21 | 3.75 | 1.58 | 40 | 8 | 4.75 | 97 | III-6 |

TABLE 18

| Compd. No. | R$^1$ | R$^2$ | m.p. (°C.) | Appearance | Solvent for Recrystalln. | Molecular Formula | Elementary Analysis (%) Up (Calcd.) Down (Found) | | | NMR (CDCl$_3$) δ |
|---|---|---|---|---|---|---|---|---|---|---|
| | | | | | | | C | H | N | |
| III-2 | 7-OMe | H | 228-230 | Colorless | AcOEt | C$_{30}$H$_{23}$N$_3$O | 81.61 / 81.32 | 5.25 / 5.34 | 9.52 / 9.48 | 3.91 (3H, s), 7.00~7.60 (17H, m), 8.01 (2H, s), 8.47 (1H, d) |
| III-3 | 8-F | H | 267-269 | Colorless | AcOEt—CH$_2$Cl$_2$ | C$_{29}$H$_{20}$N$_3$F | 81.09 / 80.67 | 4.69 / 4.96 | 9.78 / 9.66 | 7.13~7.52 (17H, m), 7.97 (1H, s), 8.03~8.23 (1H, s), 8.13 (1H, s) |
| III-4 | 7-F | H | 226-228 | Colorless | AcOEt | C$_{29}$H$_{20}$N$_3$F | 81.09 / 81.18 | 4.69 / 4.78 | 9.78 / 9.84 | 7.10~7.50 (16H, m), 7.63~7.80 (1H, m), 8.07 (1H, s), 8.10 (1H, s) 8.52~8.68 (1H, m) |
| III-5 | 8-Me | H | 270-272 | Colorless | AcOEt | C$_{30}$H$_{23}$N$_3$ | 84.68 / 84.74 | 5.45 / 5.44 | 9.87 / 9.93 | 2.60 (3H, s), 7.10~7.60 (16H, m), 7.97 (1H, d), 8.03 (2H, s), 8.37 (1H, d) |
| III-6 | 8-OMe | H | 252-254 | Colorless | AcOEt-n-hexane | C$_{30}$H$_{23}$N$_3$O | 81.61 / 81.73 | 5.25 / 5.38 | 9.52 / 9.48 | 4.00 (3H, s), 7.13~7.50 (17H, m), 7.90 (1H, d) 7.97 (1H, s), 8.03 (1H, s) |

REFERENTIAL EXAMPLE 13

2-Benzyl-8-fluoro-1H-imidazo[4,5-c]quinoline (VII-1)

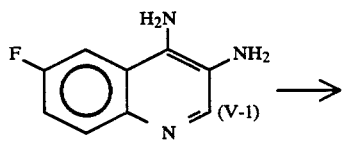

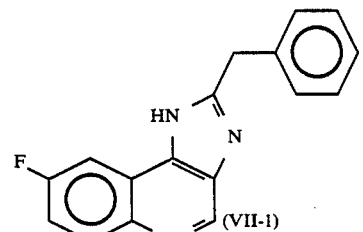

To a mixture of 10 ml of HMPA and 1 ml of MeCN was added 935 mg of phenylacetyl chloride at −10° C.

After stirring at the same temperature for 15 min., 900 mg of 3,4-diamino-6-fluoroquinoline (V-1) was added and the mixture was stirred for 3 hours at −5°∼0° C. The reaction mixture was diluted with ice water and neutralized with saturated aqueous sodium hydrogencarbonate. The crystals precipitated were collected by filtration, dissolved in 200 ml of ethyl acetate and dried. The ethyl acetate was removed and the residue was crystallized from n-hexane to give 1.44 g of the compound (VI-1). The compound (VI-1) was suspended in 50 ml of ethylene glycol and refluxed for 30 min. The mixture was concentrated under reduced pressure. Water was added to the residue. The crystals precipitated were collected by filtration, washed with water, dissolved in 70 ml of ethyl acetate and dried. The ethyl acetate was removed and the residue was crystallized from n-hexane to give 1.3 g (yield: 92%) of the titled compound (VII-1). This was recrystallized from ethyl acetate to give colorless crystals melting at 226°∼228° C.

Anal. Calcd. (%) for $C_{17}H_{12}N_3F$: C, 73.63; H, 4.36; N, 15,15; F, 6.85. Found (%): C, 73.83; H, 4.30; N, 15.13; F, 6.55.

NMR (DMSO-$d_6$) δ: 4.33 (2H, s), 7.20∼7.65 (6H, m), 7.93∼8.25 (2H, m), 9.11 (1H, s).

REFERENTIAL EXAMPLES 14–16

In the same manner as in Referential Example 13, the compounds (VII) were obtained under the reaction conditions shown in Table 19. The physical properties of the compounds were shown in Table 20-1 and 20-2.

TABLE 19

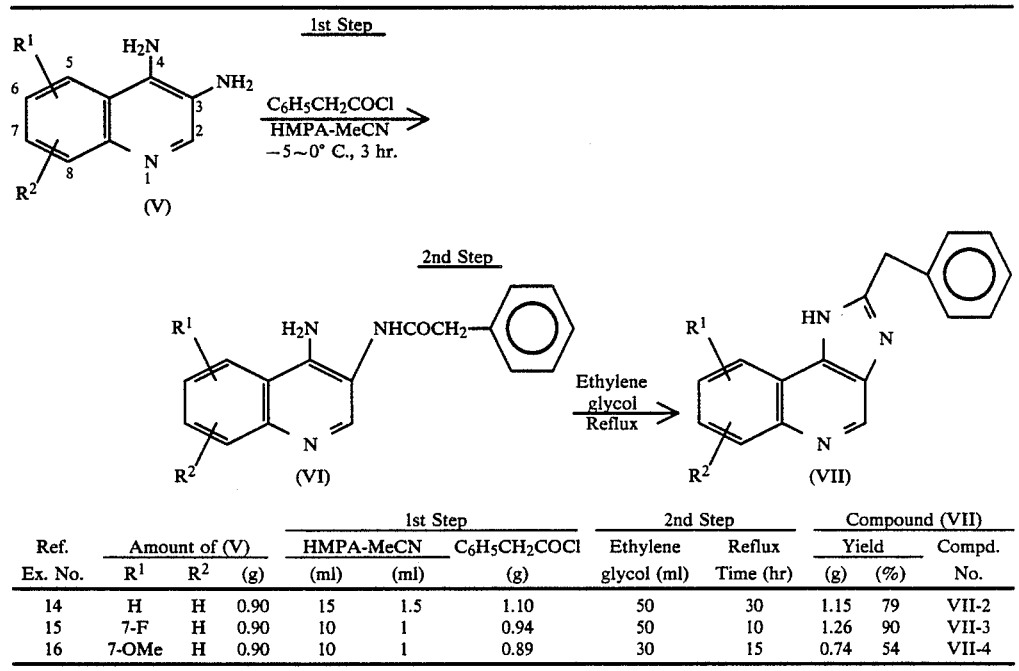

| Ref. Ex. No. | Amount of (V) R¹ | R² | (g) | 1st Step HMPA-MeCN (ml) | $C_6H_5CH_2COCl$ (ml) | (g) | 2nd Step Ethylene glycol (ml) | Reflux Time (hr) | Compound (VII) Yield (g) | (%) | Compd. No. |
|---|---|---|---|---|---|---|---|---|---|---|---|
| 14 | H | H | 0.90 | 15 | 1.5 | 1.10 | 50 | 30 | 1.15 | 79 | VII-2 |
| 15 | 7-F | H | 0.90 | 10 | 1 | 0.94 | 50 | 10 | 1.26 | 90 | VII-3 |
| 16 | 7-OMe | H | 0.90 | 10 | 1 | 0.89 | 30 | 15 | 0.74 | 54 | VII-4 |

TABLE 20

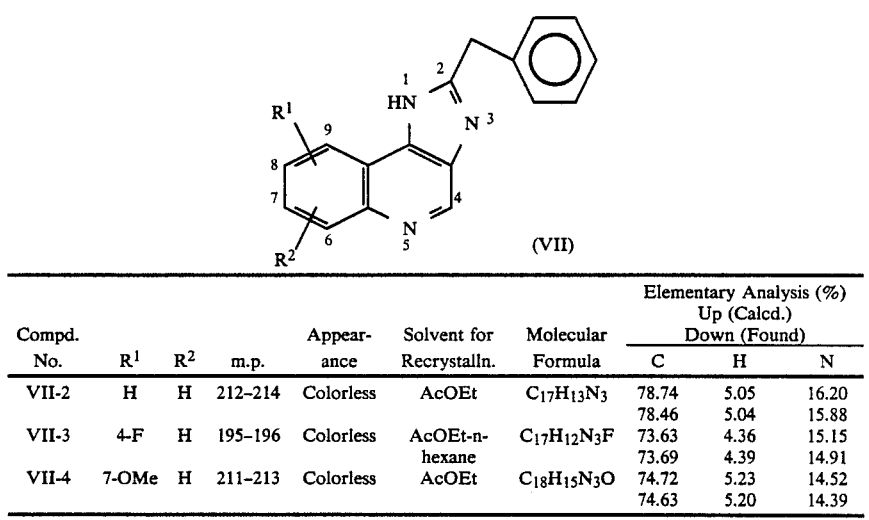

| Compd. No. | R¹ | R² | m.p. | Appearance | Solvent for Recrystalln. | Molecular Formula | Elementary Analysis (%) Up (Calcd.) Down (Found) C | H | N |
|---|---|---|---|---|---|---|---|---|---|
| VII-2 | H | H | 212–214 | Colorless | AcOEt | $C_{17}H_{13}N_3$ | 78.74 / 78.46 | 5.05 / 5.04 | 16.20 / 15.88 |
| VII-3 | 4-F | H | 195–196 | Colorless | AcOEt-n-hexane | $C_{17}H_{12}N_3F$ | 73.63 / 73.69 | 4.36 / 4.39 | 15.15 / 14.91 |
| VII-4 | 7-OMe | H | 211–213 | Colorless | AcOEt | $C_{18}H_{15}N_3O$ | 74.72 / 74.63 | 5.23 / 5.20 | 14.52 / 14.39 |

| Compound No. | NMR (DMSO-$d_6$) δ |
|---|---|
| VII-2 | 4.33(2H, s), 7.10∼7.50(5H, m), 7.53∼7.80(2H, m), 7.90∼8.50(2H, m), 9.13(1H, s) |
| VII-3 | 4.35(2H, s), 7.20∼7.47(5H, m), 7.53∼7.95(2H, m), 8.25∼8.60(1H, m), 9.17(1H, s) |

TABLE 20-continued

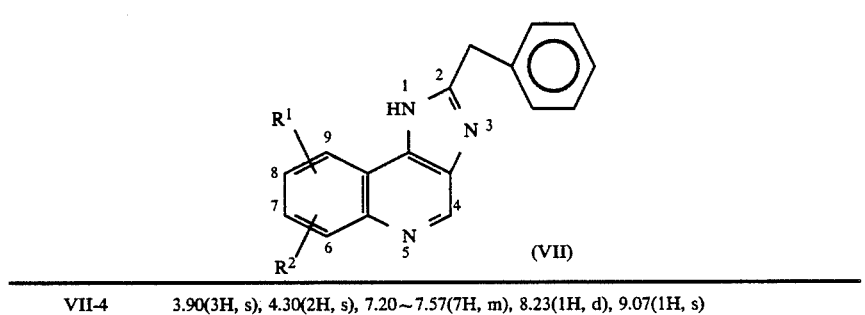

| | |
|---|---|
| VII-4 | 3.90(3H, s), 4.30(2H, s), 7.20~7.57(7H, m), 8.23(1H, d), 9.07(1H, s) |

REFERENTIAL EXAMPLE 17

4-Amino-7-fluoro-3-(trichloroacetimidoylamino)quinoline diacetate (VIII-1)

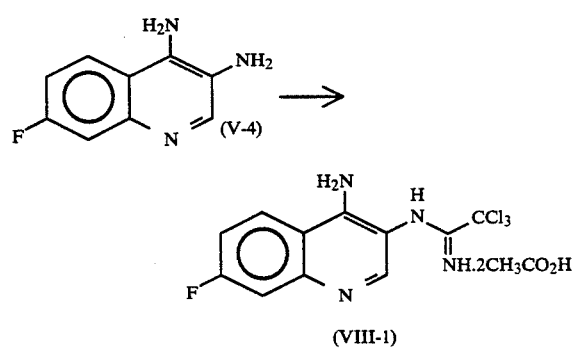

To a solution of 1.77 g of 3,4-diamino-7-fluoro-quinoline (V-4) in 20 ml of acetic acid was added 1.94 g of methyl trichloroacetimidate and the mixture was stirred for two hours at room temperature. After concentration under reduced pressure, 10 ml of ethyl acetate was added to the residue, and the mixture was allowed to stand overnight. The crystals precipitated were collected by filtration and washed with ethyl acetate and then a small quantity of ethanol to give 3.75 g (yield: 87%) of the titled compound (VIII-1).

Melting point: 120°~125° C. (d)

Anal. Calcd. (%) for $C_{15}H_{16}N_4O_4FCl_3$: C, 40.79; H, 3.65; N, 12.68; F, 4.30; Cl, 24.08. Found (%): C, 40.42; H, 3.90; N, 12.79; F, 4.40; Cl, 24.56.

NMR (DMSO-$d_6$) δ: 1.90 (6H, s), 7.20~7.60 (2H, m), 8.17 (1H, s), 8.24 (1H, m).

REFERENTIAL EXAMPLE 18

4-Amino-3-(trichloroacetimidoylamino)quinoline acetate (VIII-2)

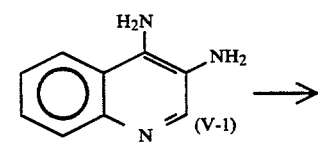

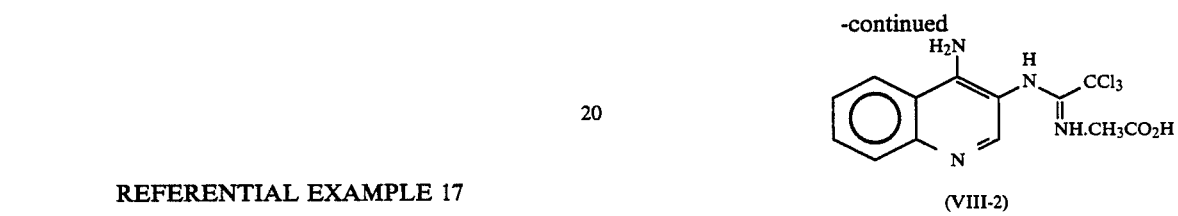

In the same manner as in Ref. Ex. 17, 1.59 g of 3,4-diaminoquinoline (V-1) in 20 ml of acetic acid was treated with 1.9 g of methyl trichloroacetimidate to give 3.13 g (yield: 80%) of the titled compound (VIII-2).

Melting point: 143°~145° C. (d)

Anal. Calcd. (%) for $C_{13}H_{13}N_4O_2Cl_3$: C, 42.93; H, 3.60; N, 15.40; Cl, 29.24. Found (%): C, 42.88; H, 3.68; N, 15.04; Cl, 29.19.

NMR (DMSO-$d_6$), δ: 1.90 (3H, s), 7.30~7.90 (3H, m), 8.13 (1H, m), 8.17 (1H, s).

REFERENTIAL EXAMPLE 19

1-Methyl-1H-imidazo[4,5-c]quinoline (II-2)

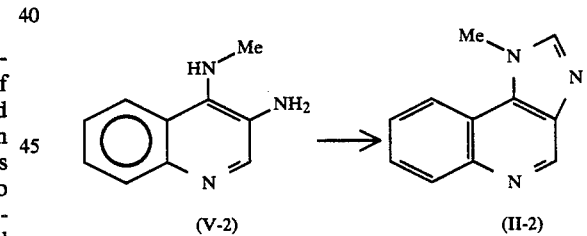

A solution of 2.92 g of 3-amino-4-methylaminoquinoline (V-2) in 20 ml of formic acid was refluxed for 1.5 hours. The reaction mixture was concentrated under reduced pressure and the residue was partitioned between chloroform and saturated aqueous sodium hydrogen-carbonate. The organic layer was washed with brine and dried. The chloroform was removed and the residue was crystallized from n-hexane to give 2.39 g (yield: 77%) of the titled compound (II-2). This was recrystallized from ethyl acetate to give colorless crystals melting at 146°~148° C.

Anal. Calcd. (%) for $C_{11}H_9N_3$: C, 72.11; H, 4.95; N, 22.94. Found (%): C, 72.25; H, 4.94; N, 22.86.

NMR (CDCl$_3$), δ: 4.20 (3H, s), 7.45~7.80 (2H, m), 7.84(1H, s), 8.15~8.40 (2H, m), 9.33 (1H, s).

EFFECT OF THE INVENTION

The compounds of the present invention show a high affinity for the benzodiazepine (BZ) receptor in brain.

The BZ receptor ligands (compounds bound to the receptor) are thought to comprise a continuous spectrum of agents with a graduated range of pharmacological efficacies at the receptor: (1) full agonists (positive efficacy; anxiolytic/anticonvulsant), (2) partial agonists, selective anxiolytic), (3) antagonists (nil efficacy; antagonism towards the other classes), (4) partial inverse agonists (intermediate negative efficacy; proconvulsant, cognition enhancer), and (5) full inverse agonists (negative efficacy; anxiogenic/convulsant). The classification can be achieved mainly on the basis of inhibition or facilitation of the pentylenetetrazole-induced convulsions [C. Braestrup et al., Biochem. Pharmcol. 33, 859 (1984)]. The inverse agonist methyl $\beta$-carbonline-3-carboxylate ($\beta$-CCM) enhances the performance in several animal models of learning and memory, whereas the agonist diazepam impairs such performance in humans, suggesting that partial inverse agonists may provide a new type of nootropic drugs [M. Sarter et al., TINS 11, 13 (1988)]. Thus, agonists are exected to work as anxiolytic or anticonvulsant agents, antagonists as antidotes for benzodiazepine intoxication and accidental excessive uptake thereof, and partial inverse agonists as cognition enhancers or nootropic agents.

Experiments of the compounds of the present invention are shown below.

EXPERIMENT 1

Test on Binding to Benzodiazepine Receptor

This test was carried out modifying partially a method of Möhler & Okada, Science, 198, 849–851 (1977). Receptor preparation was provided from the cerebral cortex of male Wistar rats (11–13 weeks age). Inhibitory action of the test compound on the specific binding of tritium-labeled diazepam to the receptor was evaluated as follows: 2 nM tritium-labeled diazepam and an aqueous solution of the test compound in 5 or 6 different concentrations were incubated with the receptor preparation at 0° C. for 60 minutes. The 50% inhibitory concentration ($IC_{50}$) was measured by the concentration-response curve. In addition, the inhibitory constant (Ki) of the test compound was calculated by dissociation constant (Kd) and concentration (L) of the tritium-labeled diazepam. The results are shown in the undermentioned table.

$$Ki = \frac{IC_{50}}{1 + \frac{L}{Kd}}$$

| Test Compound | Ki (nM) |
|---|---|
| Ic-1 | 0.357 |
| Ic-4 | 0.409 |
| Ic-6 | 0.432 |
| Ic-9 | 6.11 |
| Ic-14 | 1.24 |
| Ic-18 | 3.60 |
| Ic-21 | 0.50 |
| Ic-22 | 1.90 |
| Ic-27 | 13.1 |
| Ic-31 | 1.50 |
| Ic-37 | 2.21 |
| Ic-41 | 8.33 |
| Ic-45 | 3.20 |
| Ic-49 | 1.80 |
| Ic-50 | 0.819 |
| Ic-56 | 1.07 |
| Ic-60 | 0.373 |

EXPERIMENT 2

Anatagonism of Pentylenetetrazole-Induced Convulsion

Agonistic activity was evaluated in this Experiment. Pentylenetetrazole was subscutaneously administered male mice (a group of 8–16 male mice was employed in each test) at a dose of 125 mg/kg immediately after intravenous injection of the test compound. The dose ($ED_{50}$) required to prevent tonic convulsion and death in 50% of the animals during subsequent 2-hour observation period was calculated by the probit method.

| Test Compd. | $ED_{50}$ (mg/kg) |
|---|---|
| Ic-9 | 3.21 |
| Ic-27 | 2.47 |
| Ic-36 | 0.46 |
| Ic-38 | 1.12 |
| Ic-45 | 0.88 |
| Id-2 | 1.06 |

EXPERIMENT 3

Potentiation of Pentylenetetrazole-Induced Convulsion

Inverse agonist activity was evaluated in this Experiment. Pentylenetetrazole was subscutaneously administered male mice (a group of 8–16 male mice was employed in each test) at a dose of 90 mg/kg immediately after intravenous injection of the test compound. The dose ($ED_{50}$) required to produce tonic convulsion and death in 50% of the aminals during subsequent 2-hour observation period was calculated by the probit method.

| Test Compd. | $ED_{50}$ (mg/kg) |
|---|---|
| Ic-6 | 1.00 |
| Ic-14 | 0.20 |
| Ic-22 | 0.15 |
| Ic-24 | 0.09 |
| Ic-60 | 0.71 |
| Ic-64 | 0.31 |
| Ic-67 | 0.35 |

What we claim is:
1. A compound of the formula:

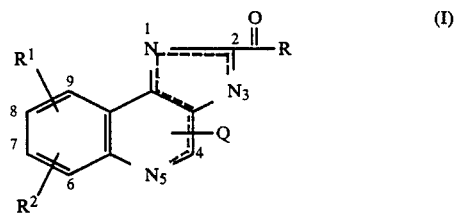

wherein R is (1) hydrogen, (2) $C_1$–$C_{10}$ alkyl optionally substituted by halogen, $C_1$–$C_5$ alkylthio, $C_1$–$C_5$ alkyloxycarbonyl, or phenyl, (3) $C_3$–$C_5$ cycloalkyl optionally substituted by $C_1$–$C_5$ alkyl, (4) $C_2$–$C_5$ alkenyl optionally substituted by $C_1$–$C_5$ alkyl or di-$C_1$–$C_5$ alkyl (5) amino optionally substituted by $C_1$–$C_5$ alkyl or di $C_1$–$C_5$ alkyl, (6) phenyl optionally substituted by one or two members independently selected from the group consisting of halogen, trifluoromethyl, $C_1$–$C_5$ alkoxy, and $C_1$–$C_5$ alkylthio, or (7) a isoxazolyl, isothiazolyl, pyrazolyl, oxazolyl, thiazolyl, imidazolyl, oxadiazolyl, thienyl, furyl or pyridyl each optionally substituted by one or two members independently selected from the group consisting of halogen, $C_1$–$C_5$ alkyl, and phenyl; Q is hydrogen, $C_1$–$C_5$ alkyl, benzyl, benzhydryl, trityl, $C_1$–$C_{13}$ acyl, $C_1$–$C_5$ alkylsulfonyl, or $C_6$–$C_{12}$ arylsulfonyl, provided that Q is located at the nitrogen atom of the 1-, 3-, or 5-position; $R^1$ and $R^2$ each is a hydrogen, $C_1$–$C_5$ alkyl, $C_1$–$C_5$ alkoxy, or halogen; and the dotted lines indicate the presence of three double bonds at positions 2(3), 3a(9b), 4(5); 1(9b), 2(3), 3a(4); or 1(2), 3a(9b), 4(5); or a pharmaceutically acceptable acid addition salt thereof.

2. A compound claimed in claim 1, namely 2-cyclopropylcarbonyl-7-fluoro-1H-imidazo[4,5-c]quinoline.

3. A compound claimed in claim 1, namely 2-cyclopropylcarbonyl-7-methoxy-1H-imidazo[4,5-c]quinoline.

4. A pharmaceutical composition for treatment of depression, convulsion, anxiety, amnesia, senile dementia, or cerebral disorder, comprising a pharmacologically effective amount of a compound according to claim 1 together with a carrier, diluent, and/or excipient.

5. A method for treating a patient suffereing from depression, convulsion, anxiety, amnesia, senile dementia, or cerebral disorder characterized by administering a pharmaceutical composition according to claim 4 to the patient.

6. A compound claimed in claim 1, namely 2-isobutyryl-7-fluoro-1H-imidazo[4,5-c]quinoline.

7. A compound claimed in claim 1, namely 2-butyryl-1H-imidazo[4,5-c]quinoline.

8. A compound claimed in claim 1, namely 2-(4-fluorobenzoyl)-1H-imidazo[4,5-c]quinoline.

* * * * *